(12) United States Patent
Jonsson et al.

(10) Patent No.: US 11,844,709 B2
(45) Date of Patent: **\*Dec. 19, 2023**

(54) ADJUSTABLE SEAL SYSTEM

(71) Applicant: Ossur Iceland ehf, Reykjavik (IS)

(72) Inventors: Grimur Jonsson, Reykjavik (IS); Linda Ros Birgisdottir, Reykjavik (IS); Arora Helgadottir, Reykjavik (IS); Unnur Osp Asgrimsdottir, Reykjavik (IS); Egill Sveinbjorn Egilsson, Reykjavik (IS)

(73) Assignee: OSSUR ICELAND EHF, Reykjavik (IS)

( * ) Notice: Subject to any disclaimer, the term of this patent is extended or adjusted under 35 U.S.C. 154(b) by 62 days.

This patent is subject to a terminal disclaimer.

(21) Appl. No.: 16/577,496

(22) Filed: Sep. 20, 2019

(65) Prior Publication Data

US 2020/0008961 A1 Jan. 9, 2020

Related U.S. Application Data

(63) Continuation of application No. 15/284,731, filed on Oct. 4, 2016, now Pat. No. 10,420,657.

(Continued)

(51) Int. Cl.
*A61F 2/78* (2006.01)
*A61F 2/80* (2006.01)
(Continued)

(52) U.S. Cl.
CPC .............. *A61F 2/80* (2013.01); *A61F 2/7812* (2013.01); *A61F 2002/5072* (2013.01);
(Continued)

(58) Field of Classification Search
CPC ... A61F 2/78; A61F 2/7812; A61F 2/80; F16J 15/3452; F16J 15/3216; F16J 15/3208; F16J 15/3212; F16J 15/3224
See application file for complete search history.

(56) References Cited

U.S. PATENT DOCUMENTS

| 980,457 A | 1/1911 | Toles |
| 1,398,824 A | 11/1921 | Abrams |

(Continued)

FOREIGN PATENT DOCUMENTS

| AT | 369 978 B | 2/1983 |
| DE | 484 363 C | 10/1929 |

(Continued)

OTHER PUBLICATIONS

Eshraghi et al., "Gait Biomechanics of Individuals with Transtibial Amputation: Effect of Suspension System," PLOS ONE, vol. 9, Issue. 5, May 2014, 12 Pages.

(Continued)

*Primary Examiner* — Marcia L Watkins
(74) *Attorney, Agent, or Firm* — WORKMAN NYDEGGER

(57) ABSTRACT

An adjustable seal system includes a suspension liner having a liner body and an outer surface. A plurality of seal bands are located along a height of the liner body. A seal component is arranged for removably securing to the liner body. The seal component includes open upper and lower ends defining an opening therethrough and an internal surface arranged to frictionally engage at least one of the seal bands and secure on the outer surface of the liner. The seal component also includes an upper portion descending to at least one seal, and a lower portion.

4 Claims, 14 Drawing Sheets

Related U.S. Application Data

(60) Provisional application No. 62/241,874, filed on Oct. 15, 2015.

(51) Int. Cl.
  *F16J 15/02* (2006.01)
  *A61F 2/50* (2006.01)
  *A61F 2/68* (2006.01)
  *F16J 15/3208* (2016.01)
  *F16J 15/3212* (2016.01)
  *F16J 15/3224* (2016.01)

(52) U.S. Cl.
  CPC . *A61F 2002/6863* (2013.01); *A61F 2002/802* (2013.01); *A61F 2230/0067* (2013.01); *A61F 2230/0069* (2013.01); *F16J 15/022* (2013.01); *F16J 15/3208* (2013.01); *F16J 15/3212* (2013.01); *F16J 15/3224* (2013.01)

(56) References Cited

U.S. PATENT DOCUMENTS

| | | |
|---|---|---|
| 1,893,853 A | 1/1933 | Tullis |
| 2,267,930 A * | 12/1941 | Leonard, Jr. ......... F16J 15/3212 277/575 |
| 2,325,656 A | 8/1943 | Brophy |
| 2,464,443 A | 3/1949 | Ganoe et al. |
| 2,530,285 A | 11/1950 | Catranis |
| 2,533,404 A | 12/1950 | Sharp et al. |
| 2,634,424 A | 4/1953 | O'Gorman |
| 2,671,225 A | 3/1954 | Schoene et al. |
| 2,689,351 A | 9/1954 | Schindler |
| 2,808,593 A | 10/1957 | Andersen |
| 3,393,407 A | 7/1968 | Kandel |
| 3,587,572 A | 6/1971 | Evans |
| 3,671,980 A | 6/1972 | Baird |
| 3,947,897 A | 4/1976 | Owens |
| 4,128,903 A | 12/1978 | Marsh et al. |
| 4,215,679 A | 8/1980 | Rustin |
| 4,311,317 A | 1/1982 | Bartels |
| 4,319,413 A | 3/1982 | Mattil |
| 4,347,204 A | 8/1982 | Takagi et al. |
| 4,474,573 A | 10/1984 | Detty |
| 4,635,626 A | 1/1987 | Lerman |
| 4,738,249 A | 4/1988 | Linman et al. |
| 4,767,735 A | 8/1988 | Ewen et al. |
| 4,885,828 A | 12/1989 | Kozlowski |
| 4,908,037 A | 3/1990 | Ross |
| 4,923,474 A | 5/1990 | Klasson et al. |
| 5,007,937 A | 4/1991 | Fishman et al. |
| 5,055,528 A | 10/1991 | Kioka et al. |
| 5,108,456 A | 4/1992 | Coonan, III |
| 5,122,583 A | 6/1992 | Ewen et al. |
| 5,139,523 A | 8/1992 | Paton et al. |
| 5,163,965 A | 11/1992 | Rasmusson et al. |
| 5,169,161 A | 12/1992 | Jones |
| 5,226,918 A | 7/1993 | Silagy et al. |
| 5,244,716 A | 9/1993 | Thornton et al. |
| 5,314,496 A | 5/1994 | Harris et al. |
| 5,376,129 A | 12/1994 | Faulkner et al. |
| 5,376,131 A | 12/1994 | Lenze et al. |
| 5,387,245 A | 2/1995 | Fay et al. |
| 5,549,709 A | 8/1996 | Caspers |
| 5,571,208 A | 11/1996 | Caspers |
| 5,571,209 A | 11/1996 | Brown, Sr. |
| 5,593,454 A | 1/1997 | Helmy |
| 5,658,353 A | 8/1997 | Layton |
| 5,702,489 A | 12/1997 | Slemker |
| 5,718,925 A | 2/1998 | Kristinsson et al. |
| 5,728,168 A | 3/1998 | Laghi et al. |
| 5,728,170 A | 3/1998 | Becker et al. |
| 5,735,906 A | 4/1998 | Caspers |
| 5,830,237 A | 11/1998 | Kania |
| 5,885,674 A | 3/1999 | Maemoto et al. |
| 5,888,216 A | 3/1999 | Haberman |
| 5,888,230 A | 3/1999 | Helmy |
| 5,904,722 A | 5/1999 | Caspers |
| 5,931,872 A | 8/1999 | Lohmann |
| 5,972,036 A | 10/1999 | Kristinsson et al. |
| 5,980,577 A | 11/1999 | Radis et al. |
| 6,076,284 A | 6/2000 | Terlizzi |
| 6,136,039 A | 10/2000 | Kristinsson et al. |
| 6,149,691 A | 11/2000 | Fay et al. |
| 6,171,431 B1 | 1/2001 | Gallagher, Jr. et al. |
| 6,231,616 B1 | 5/2001 | Helmy |
| 6,231,617 B1 | 5/2001 | Fay |
| 6,273,918 B1 | 8/2001 | Yuhasz et al. |
| 6,287,345 B1 | 9/2001 | Slemker et al. |
| 6,361,568 B1 | 3/2002 | Hoerner |
| 6,368,357 B1 | 4/2002 | Schon et al. |
| 6,406,499 B1 | 6/2002 | Kania |
| 6,468,938 B1 | 10/2002 | Govoni et al. |
| 6,485,776 B2 | 11/2002 | Janusson et al. |
| 6,508,842 B1 | 1/2003 | Caspers |
| 6,544,292 B1 | 4/2003 | Laghi |
| 6,554,868 B1 | 4/2003 | Caspers |
| 6,585,774 B2 | 7/2003 | Dean, Jr. et al. |
| 6,592,539 B1 | 7/2003 | Einarsson et al. |
| 6,626,952 B2 | 9/2003 | Janusson et al. |
| 6,645,253 B2 | 11/2003 | Caspers |
| 6,706,364 B2 | 3/2004 | Janusson et al. |
| 6,726,726 B2 | 4/2004 | Caspers |
| 6,761,742 B2 | 7/2004 | Caspers |
| 6,852,269 B2 | 2/2005 | Eberle et al. |
| 6,926,742 B2 | 8/2005 | Caspers et al. |
| 6,929,125 B1 | 8/2005 | Seamans |
| 6,964,688 B1 | 11/2005 | Kania |
| 7,001,563 B2 | 2/2006 | Janusson et al. |
| 7,025,793 B2 | 4/2006 | Gilsson |
| 7,118,602 B2 | 10/2006 | Bjarnason |
| 7,144,429 B2 | 12/2006 | Carstens |
| 7,169,188 B2 | 1/2007 | Carstens |
| 7,169,189 B2 | 1/2007 | Bjarnason et al. |
| 7,235,108 B2 | 6/2007 | Carstens |
| 7,291,182 B1 | 11/2007 | Kania |
| 7,351,264 B2 | 4/2008 | Wilson |
| 7,427,297 B2 | 9/2008 | Patterson et al. |
| 7,592,286 B2 | 9/2009 | Morini et al. |
| 7,749,281 B2 | 7/2010 | Egilsson |
| 7,771,487 B2 | 8/2010 | Mantelmacher |
| 7,909,884 B2 | 3/2011 | Egilsson et al. |
| 8,034,120 B2 | 10/2011 | Egilsson et al. |
| 8,052,760 B2 | 11/2011 | Egilsson et al. |
| 8,097,043 B2 | 1/2012 | Egilsson |
| 8,206,459 B1 | 6/2012 | Lock et al. |
| 8,372,159 B2 | 2/2013 | Mackenzie |
| 8,956,422 B2 | 2/2015 | Halldorsson |
| 9,603,726 B2 | 3/2017 | Egilsson et al. |
| 9,707,106 B2 | 7/2017 | Egilsson et al. |
| 9,877,851 B2 | 1/2018 | Egilsson et al. |
| 2001/0005798 A1 | 6/2001 | Caspers |
| 2001/0016781 A1 | 8/2001 | Caspers |
| 2002/0040248 A1 | 4/2002 | Karason |
| 2002/0087215 A1 | 7/2002 | Caspers |
| 2002/0091449 A1 | 7/2002 | Caspers et al. |
| 2002/0099450 A1 | 7/2002 | Dean, Jr. et al. |
| 2002/0165619 A1 | 11/2002 | Hellberg |
| 2002/0183859 A1 | 12/2002 | Iouser |
| 2003/0181989 A1 | 9/2003 | Eberle et al. |
| 2003/0191539 A1 | 10/2003 | Caspers |
| 2004/0012158 A1 | 1/2004 | Neuhaus |
| 2004/0024322 A1 | 2/2004 | Caspers |
| 2004/0030411 A1 | 2/2004 | Caspers |
| 2004/0040248 A1 | 3/2004 | Vilnes |
| 2004/0098136 A1 | 5/2004 | Caspers |
| 2004/0122528 A1 | 6/2004 | Egilsson |
| 2004/0143345 A1 | 7/2004 | Caspers |
| 2004/0167638 A1 | 8/2004 | Caspers |
| 2004/0181290 A1 | 9/2004 | Caspers |
| 2004/0236434 A1 | 11/2004 | Carstens |
| 2004/0243251 A1 | 12/2004 | Carstens |
| 2004/0243252 A1 | 12/2004 | Carstens |
| 2005/0101693 A1 | 5/2005 | Arbogast et al. |

(56) References Cited

U.S. PATENT DOCUMENTS

| | | |
|---|---|---|
| 2005/0216095 A1 | 9/2005 | Egilsson |
| 2005/0240282 A1 | 10/2005 | Rush et al. |
| 2005/0240283 A1 | 10/2005 | Kania |
| 2005/0267598 A1 | 12/2005 | Bjarnason et al. |
| 2005/0267599 A1 | 12/2005 | Bjarnason |
| 2006/0212128 A1 | 9/2006 | Nachbar |
| 2006/0293762 A1 | 12/2006 | Schulman et al. |
| 2007/0005149 A1 | 1/2007 | Egilsson et al. |
| 2007/0021295 A1 | 1/2007 | Morini et al. |
| 2007/0027556 A1 | 2/2007 | Wilson |
| 2007/0043450 A1 | 2/2007 | Pickering et al. |
| 2007/0061017 A1 | 3/2007 | Wilson |
| 2007/0123998 A1 | 5/2007 | Egilsson et al. |
| 2007/0179606 A1 | 8/2007 | Huyghe et al. |
| 2008/0086218 A1 | 4/2008 | Egilsson |
| 2008/0147202 A1 | 6/2008 | Danzig et al. |
| 2008/0188949 A1 | 8/2008 | Mackenzie |
| 2008/0221705 A1 | 9/2008 | Scussel |
| 2008/0221706 A1 | 9/2008 | Scussel et al. |
| 2008/0269914 A1 | 10/2008 | Coppens et al. |
| 2009/0036999 A1 | 2/2009 | Egilsson et al. |
| 2009/0069171 A1 | 3/2009 | Sagae |
| 2009/0157196 A1 | 6/2009 | Danzig et al. |
| 2009/0182435 A1 | 7/2009 | Haberman |
| 2009/0198346 A1 | 8/2009 | Perkins et al. |
| 2009/0240344 A1 | 9/2009 | Colvin et al. |
| 2009/0306791 A1 | 12/2009 | Slemker et al. |
| 2010/0070051 A1 | 3/2010 | Carstens |
| 2010/0185300 A1 | 7/2010 | Mackenzie |
| 2010/0249950 A1 | 9/2010 | Bielefeld |
| 2010/0274364 A1 | 10/2010 | Pacanowsky et al. |
| 2010/0318196 A1 | 12/2010 | Egilsson |
| 2011/0029096 A1 | 2/2011 | Laghi |
| 2011/0035027 A1 | 2/2011 | Mccarthy |
| 2011/0054635 A1 | 3/2011 | Watts |
| 2011/0071649 A1 | 3/2011 | Mckinney |
| 2011/0077748 A1 | 3/2011 | Egilsson et al. |
| 2011/0118854 A1 | 5/2011 | Halldorsson |
| 2011/0156361 A1* | 6/2011 | Ghalambor .......... F16J 15/3452 277/589 |
| 2012/0041568 A1 | 2/2012 | Mackenzie |
| 2012/0095571 A1 | 4/2012 | Gunnarsson et al. |
| 2013/0053982 A1 | 2/2013 | Halldorsson |
| 2013/0138224 A1 | 5/2013 | Mackenzie |
| 2013/0197670 A1 | 8/2013 | Mackenzie |
| 2013/0331952 A1 | 12/2013 | Halldorsson et al. |
| 2015/0142133 A1 | 5/2015 | Egilsson et al. |
| 2015/0202060 A1 | 7/2015 | Muller et al. |
| 2017/0261108 A1* | 9/2017 | Soler .................... F16J 15/3208 |
| 2017/0304085 A1 | 10/2017 | Kurth |

FOREIGN PATENT DOCUMENTS

| | | |
|---|---|---|
| DE | 745 981 C | 5/1944 |
| DE | 813 190 C | 9/1951 |
| DE | 1 795 809 U | 9/1959 |
| DE | 2 060 239 A1 | 6/1972 |
| DE | 2 127 269 A1 | 12/1972 |
| DE | 2 540 138 A1 | 3/1977 |
| DE | 2 544 446 A1 | 4/1977 |
| DE | 3 221 920 A1 | 4/1983 |
| DE | 3 508 919 A1 | 9/1986 |
| DE | 9 419 208 U1 | 1/1995 |
| EP | 0 631 765 A1 | 1/1995 |
| EP | 1 572 043 A2 | 9/2005 |
| EP | 2353550 A1 | 8/2011 |
| EP | 2745807 A1 | 6/2014 |
| EP | 2815728 A1 | 12/2014 |
| FR | 2 420 335 A1 | 10/1979 |
| FR | 2 539 616 A1 | 7/1984 |
| FR | 2 828 093 A1 | 2/2003 |
| GB | 263 377 A | 12/1926 |
| GB | 267 988 A | 3/1927 |
| GB | 269606 A | 4/1927 |
| GB | 826 041 A | 12/1959 |
| GB | 2 069 847 A | 9/1981 |
| GB | 2 087 727 A | 6/1982 |
| JP | H0623406 A | 2/1994 |
| JP | H07109314 A | 4/1995 |
| JP | H7-155343 A | 6/1995 |
| JP | H9-104714 A | 4/1997 |
| JP | 2637076 B2 | 8/1997 |
| JP | 2740503 B2 | 4/1998 |
| JP | H10-182740 A | 7/1998 |
| JP | 2001-055413 A | 2/2001 |
| JP | 2002-500697 A | 1/2002 |
| JP | 2006-176565 A | 7/2006 |
| JP | 2006-316160 A | 11/2006 |
| JP | 2006-528271 A | 12/2006 |
| JP | 3984304 B2 | 10/2007 |
| JP | 2011206118 A | 10/2011 |
| WO | 97/34548 A2 | 9/1997 |
| WO | 9734548 A2 | 9/1997 |
| WO | 00/74611 A2 | 12/2000 |
| WO | 01/54631 A1 | 8/2001 |
| WO | 01/67842 A1 | 9/2001 |
| WO | 02/26158 A2 | 4/2002 |
| WO | 03/024367 A2 | 3/2003 |
| WO | 03/024370 A1 | 3/2003 |
| WO | 03/039398 A2 | 5/2003 |
| WO | 03/099173 A1 | 12/2003 |
| WO | 2004/060136 A2 | 7/2004 |
| WO | 2010/085336 A1 | 7/2010 |
| WO | 2013/005735 A1 | 1/2013 |
| WO | 2015073793 A1 | 5/2015 |

OTHER PUBLICATIONS

Eshraghi et al., "Pistoning Assessment in Lower Limb Prosthetic Sockets," Prosthetics and Orthotics International, vol. 36, No. 1, 2012, pp. 15-24.

Gholizadeh et al., "Transtibial Prosthesis Suspension Systems: Systematic Review of Literature," Clinical Biomechanics vol. 29, 2014, pp. 87-97.

"Slick Sil Lsr," Surface Solutions Group LLC, retrieved from www.surfacesolutionsgroup.com on Mar. 30, 2017, 1 Page.

"Prosthetics Product Catalogue", Medi Prosthetics, www.medi-prosthetics.com, Jan. 2016, 184 pages.

"Verwendung und Verklebung Des LITE Vakuum-Ringes 5W700: Usage and Gluing of the 5W700 Lite Vacuum Ring," Wagner Polymertechnik GMBH, Sep. 6, 2016, 4 Pages.

International Search Report from PCT Application No. PCT/US2017/029063, dated Jul. 21, 2017.

International Search Report and Written Opinion from PCT Application No. PCT/US2018/058624, dated Feb. 11, 2019.

International Search Report from PCT Application No. PCT/US2016/055269, dated Jan. 4, 2017.

"Silicone-Only Suspension (SOS) with Socket-Loc and the Ring for the Lower Limb", found at, http://www.oandp.org/ipo/library/1995_01_002.asp. Journal of Prosthetics and Orthotics 1995; vol. 7, No. 1, p. 2.

Iceross Comfort Locking/Cushion Product Information Brochure, Mar. 27, 2009, 3 Pages.

Iceross Dermo, Product Information Sheets from Internet, http://www.ossur.com/prosthetics/liners/dermo, Mar. 27, 2009, 2 Sheets.

Military inStep: Prosthetic Socks and Liners, Product Information Sheets from Internet, http://www.amputee-coalition.org/military-instep/prosthetic-socks, Mar. 27, 2009, 3 Pages.

Prosthetic & Orthotic Update NewsLetter, No. 32, Internet Search Conducted Mar. 27, 2009, 4 Pages.

Walopur Platilon U, Product Information Brochure of Epurex Films GmbH & Co., KG, Internet Search Result Conducted Mar. 27, 2009, 2 Pages.

International Search Report and Written Opinion Issued in PCT/US2012/051645, dated Dec. 3, 2012.

Supplementary EP Search Report from EP Application No. 07837275.2, dated Feb. 19, 2014, 6 pages.

Extended European Search Report from EP Application No. 14161004.8, dated May 22, 2014, 6 pages.

(56) References Cited

OTHER PUBLICATIONS

Extended European Search Report from Corresponding Application No. 14163512.8, dated Jul. 30, 2014.
ESP Opti-Seal, Product Installation Instructions, http://www.wearesp.com, Downloaded Dec. 12, 2014, 1 page.
ESP Opti-Seal, "The Most Versatile Suspension System Availiable", www.wearesp.com, Downloaded Dec. 12, 2014, 2 pages.
ESP Secure-Ring System (SRS), http://www.wearesp.com, Downloaded Dec. 12, 2014, 1 page.
ESP Secure-Ring System (SRS), Product Instructions Sheet, http://www.wearesp.com, downloaded Dec. 12, 2014, 2 pages.

* cited by examiner

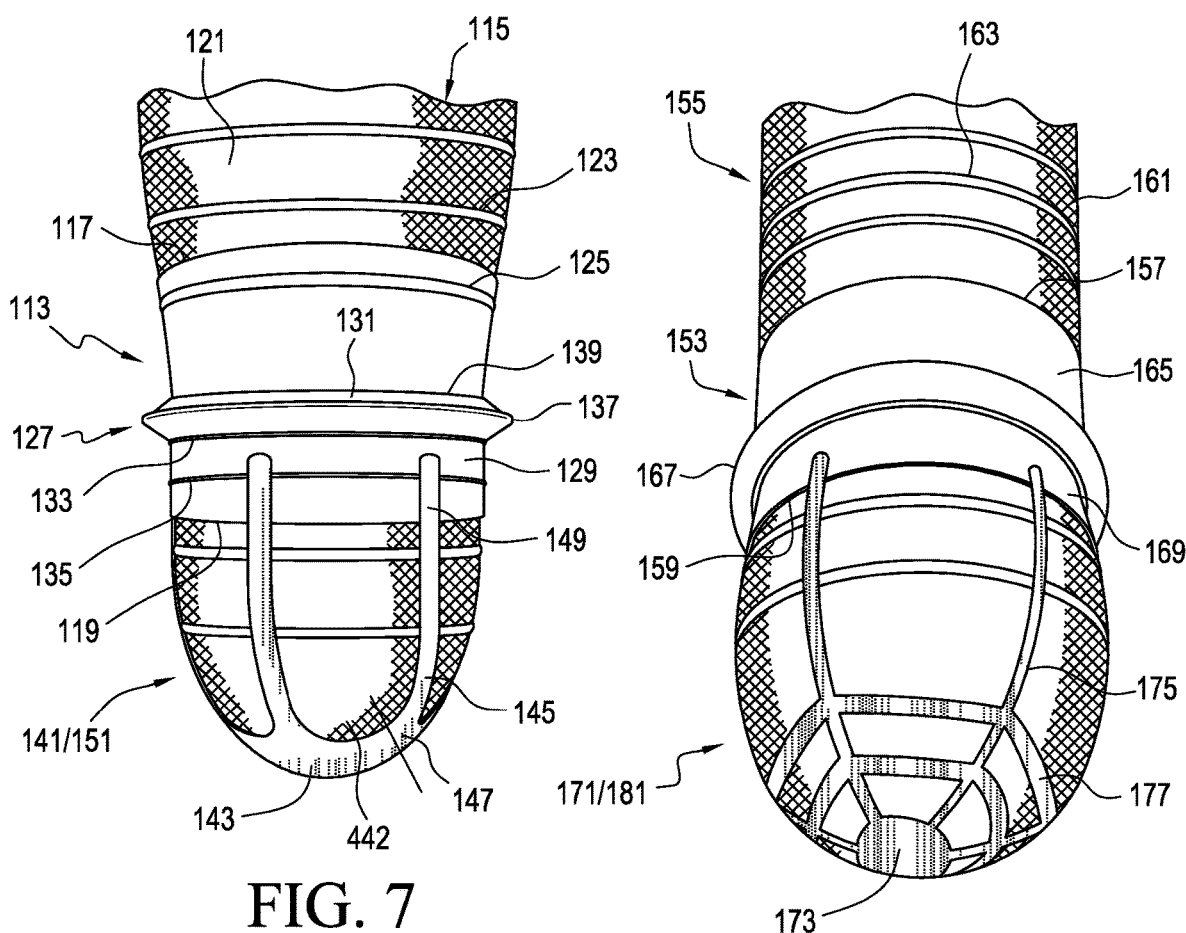
FIG. 7
FIG. 8
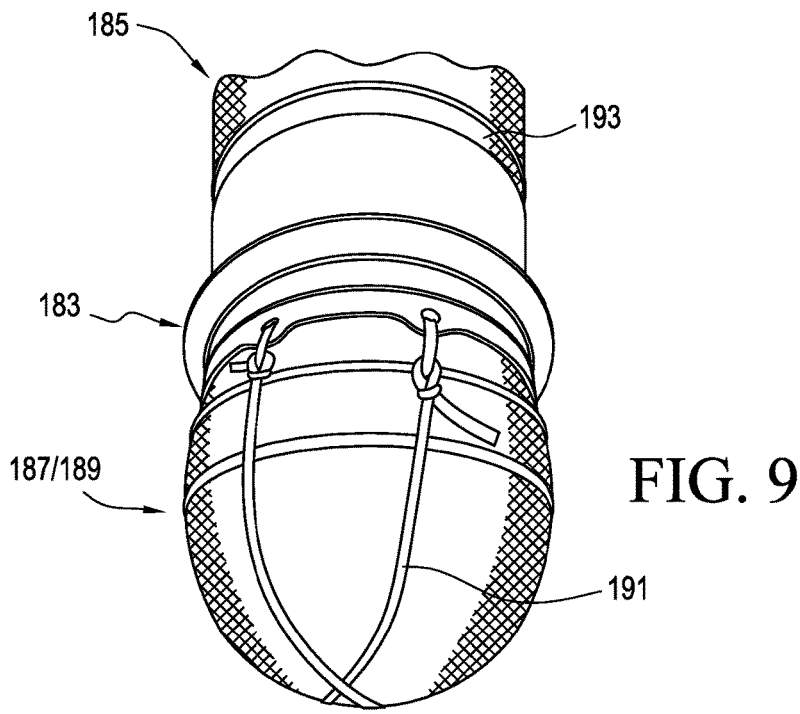
FIG. 9

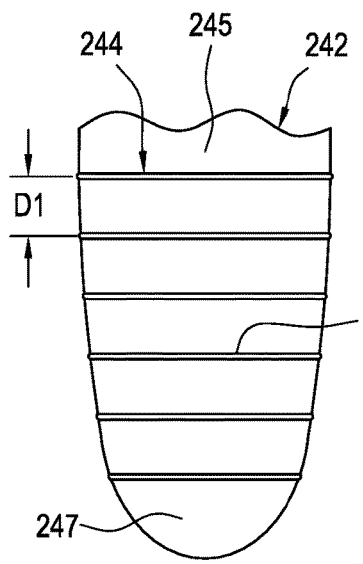 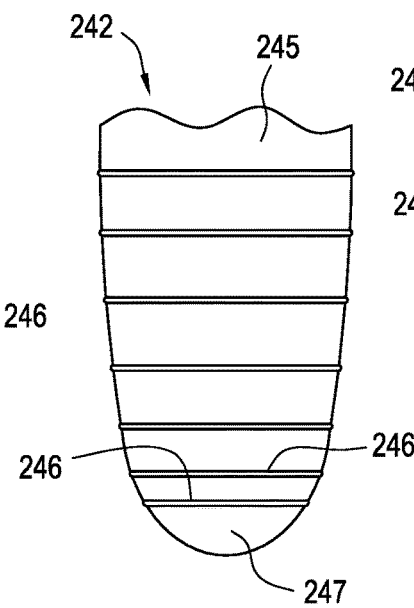 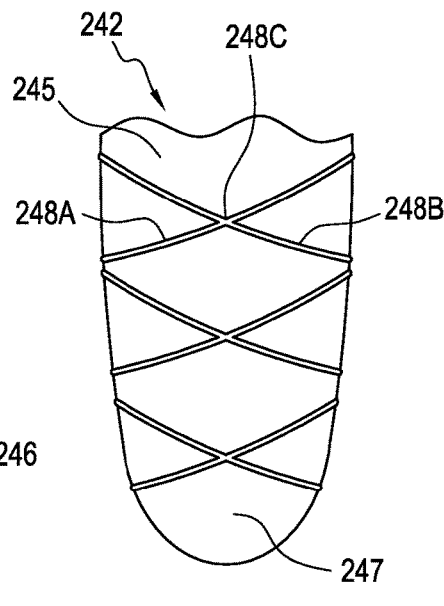
FIG. 19  FIG. 20  FIG. 21
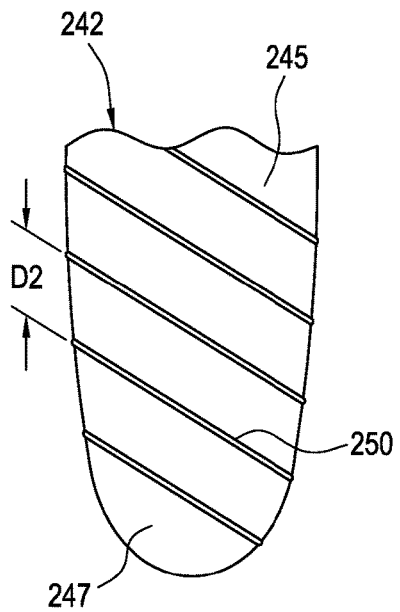 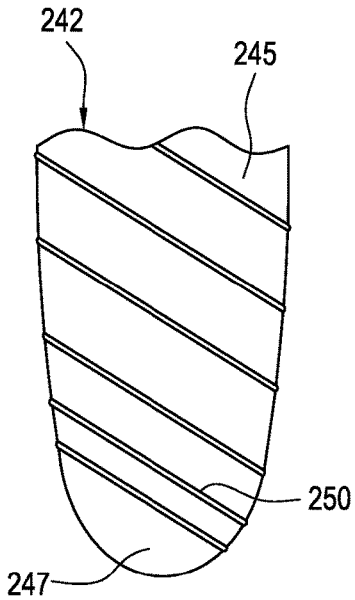 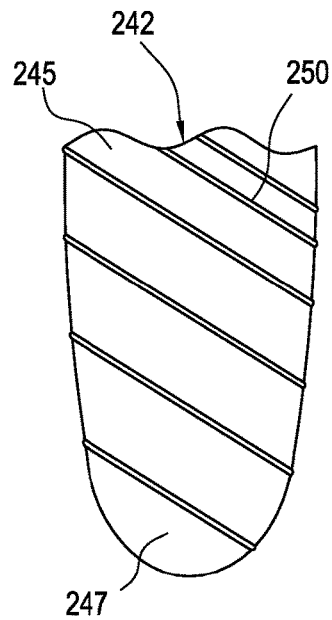
FIG. 22  FIG. 23  FIG. 24

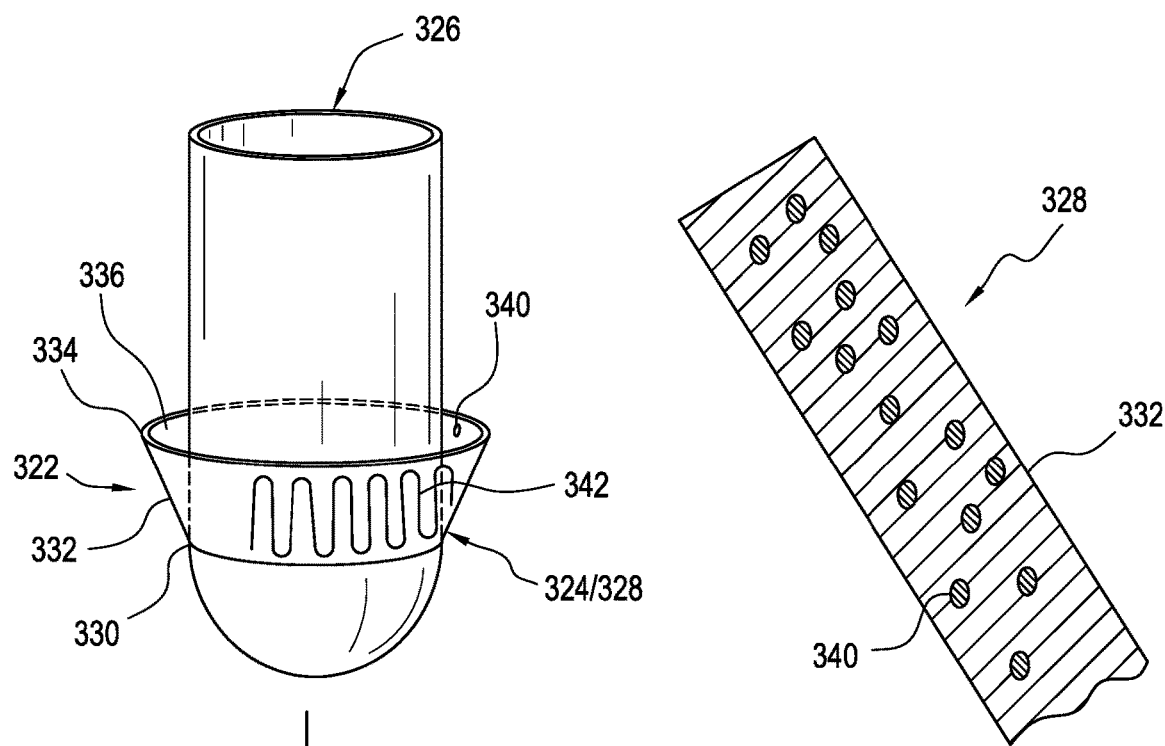
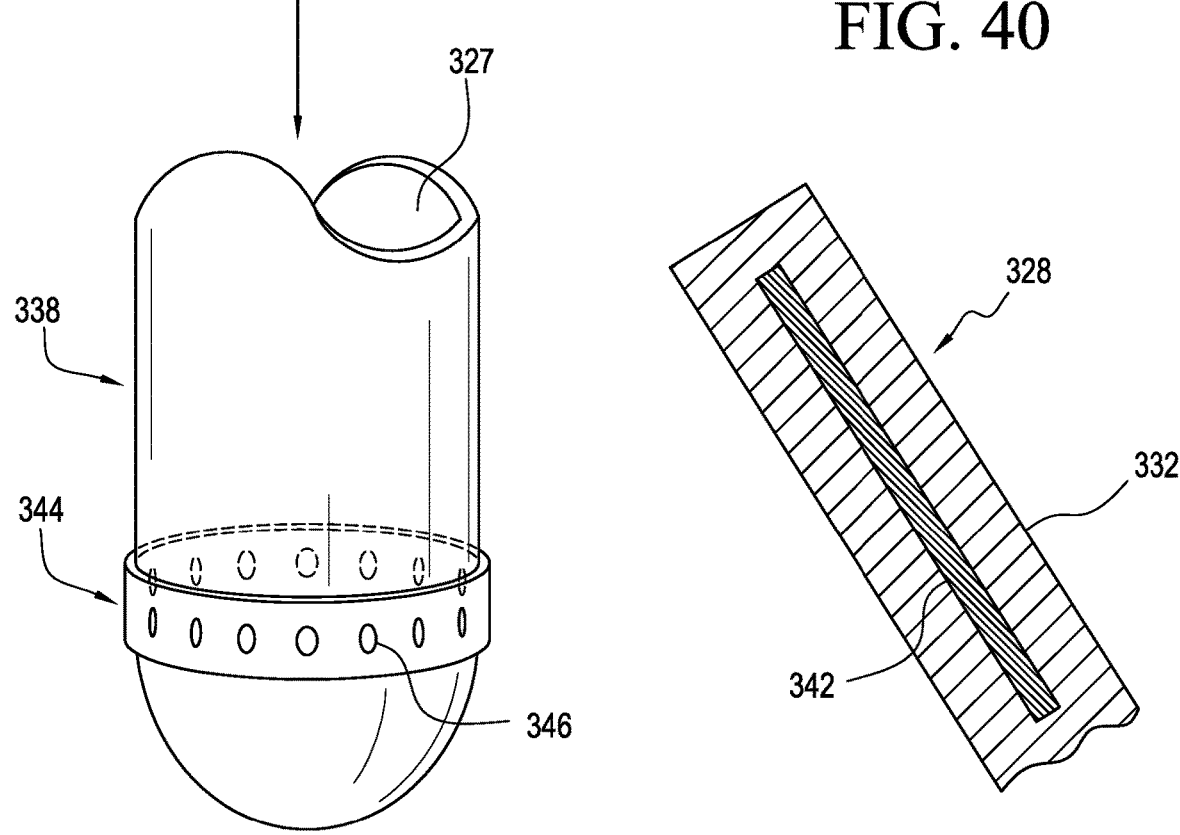
FIG. 39
FIG. 40
FIG. 41

ADJUSTABLE SEAL SYSTEM

TECHNICAL FIELD

The disclosure relates to an adjustable seal system for providing a sealing interface between a residual limb and a prosthetic socket.

BACKGROUND

Suspension liners provide a soft, flexible interface between a residual limb of an amputee and a hard socket to which a prosthetic device is secured. These liners are typically made of an air impermeable elastomer material and may include a reinforcement layer intermediate the inner and outer surfaces of the liner body or externally thereof to provide resistance against axial elongation of the elastomer constituting the liner body. Such reinforcement typically does not restrict radial distension or stretching of the liner body.

The liners may also include an outer covering different from the elastomeric material, and exemplary outer coverings include various textiles having different stretchability properties. For example, the outer cover may be a strong and stretchable nylon outer cover providing resistance to extreme wear and tear, and affording strength and durability. The nylon outer cover may be used to increase radial stretch and comfortable elasticity.

In the prior art, liners may function to secure the residual limb within a prosthetic socket once the residual limb and sleeve are inserted into the socket in a close-fitting relationship by isolating the distal end area of the hard socket from atmosphere. Upon application of a pulling force on the liner relative to the socket, suction is created in the distal end of the socket tending to retain the liner within the socket. Appropriate devices are usually provided to enable expulsion of air between the distal end of the liner and the hard socket, and to isolate the distal end of the hard socket from atmosphere after the liner with the residual limb has been fully inserted within the socket.

In some applications, the liner is provided with an umbrella at its distal end and a threaded socket for receiving a securing pin member which then extends through an axial opening in the distal end of the hard socket for securing the hard socket relative to a prosthetic device mounted to the distal end of the socket. In other applications, the prosthetic device is secured to the exterior of the distal end of the hard socket and the sleeve member is fully contained within the hard socket.

In other applications, it may be desired to more positively secure the liner within the hard socket by creating a hypobaric (vacuum) pressure within the distal end of the hard socket between such distal end and the distal end of a liner inserted into the hard socket with a residual limb contained within the liner. The hypobaric pressure may be maintained at the distal end of the hard socket and the interior of the socket at its distal end will be isolated from atmosphere during normal retention of the liner within the hard socket. Opening the distal end of the socket to atmosphere releases the vacuum or hypobaric pressure within the socket to enable simple withdrawal of a residual limb with a liner thereon from the socket.

A pump or other device may be utilized to evacuate the distal end of the socket between the distal end of the liner and the distal end of the socket. A valve or other appropriate device typically is used to open and close the distal end of a socket to surrounding atmosphere.

Various arrangements are known for providing an appropriate seal between the exterior of the liner and the interior of the hard socket including external air impermeable sleeves covering the interface area between the proximal area of the hard socket and the adjacent liner body.

In trans-femoral applications, the sealing between a sleeve and a socket is generally simpler and easier to execute than sealing a trans-tibial liner against the inner surface of the socket because in the latter situation, the residual limb contains more bony protuberances and irregular shapes that are difficult to effectively seal, particularly if it is desired to simply use the material of the elastomeric liner as the sealing element.

Some users find that known liners having sealing means fail to sufficiently tolerate volume fluctuations, and may leave pressure marks on the residual limb after a period of sustained use. Additional improvements may be required for some users in that known liners do not adequately conform to the user's anatomy, and therefore fail to provide necessary comfort and skin protection. Moreover, as with all suspension liners having sealing means, it is necessary that the liner provides reliable suspension after an initial phase of volume and shape conditioning after the liner is donned on the user's residual limb.

SUMMARY

The disclosure provides various embodiments of an adjustable seal system, seal components for use in the system, and methods for providing a sealing interface between a residual limb and a prosthetic socket. The embodiments are beneficial to address the challenges faced by amputees by providing flexibility in placement of a seal component to avoid various pressure points and accommodate the shape of the residual limb.

According to an embodiment, an adjustable seal system includes a suspension liner having a liner body and a plurality of seal bands, and a seal component for removably securing to the liner body. The seal component has open and lower ends defining an opening therethrough and an internal surface arranged to frictionally engage at least one of the seal bands and secure to an outer surface of the liner. The seal component also has an upper portion descending to at least one seal and a lower portion.

The adjustable seal system permits optimal seal placement rather than a permanently fixed seal placement as found in many prior art seal systems. The seal components may be located away from undercuts or shape irregularities defined by a residual limb. The seal height may be decided according to the user's needs, and the seal may be moved to adapt to various volume changes of the residual limb. The adjustable seal system embodiments require less effort when donning the liner. For example, rather than deal with a permanent seal resisting donning, the liner may be donned and then the seal may be selectively placed along the height of the liner worn by the user.

According to a variation, a distal capture system is located at the lower portion of the seal component. The distal capture system is arranged to create a connection between the seal component and a distal end of the liner after the liner is donned. The distal capture system can thus control or help set the position of the at least one seal with respect to the liner body when the seal component is installed on the liner and the distal end of the liner engages a distal end of the distal capture system, facilitating proper positioning of the seal component with respect to the liner body. This beneficially assists with seal placement for new or elderly users who may be unsure or unaware of the proper seal placement, making the seal component easier to use. Further, the distal capture system can reduce the number of fine hand movements needed to locate and/or adjust the seal component during use.

According to a variation, the distal capture system includes a distal cup member defining a plurality of longitudinal slots distributed circumferentially about the distal cup member. This allows portions of the liner body to enter the slots, improving the connection between the seal component and the liner. The slots can also beneficially influence the axial and/or radial stiffness of the distal cup member and provide improved proprioception.

According to a variation, the distal capture system includes at least one section formed of an elastic material. In use, the seal component can be installed on the liner until the distal end of the liner engages the distal end of the distal capture system. In this position, the distal capture system can provide a reference point or visual indication that the seal component is in a first or lowermost position with respect to the liner body and/or the at least one seal band.

The elasticity of the distal capture system can allow for some proximal movement of the seal component away from the distal end of the liner but such movement is limited as the distal capture system becomes taut or reaches its elastic limit, thereby restricting and/or controlling upward movement of the seal component.

When the distal capture system reaches its elastic limit, the distal capture system provides a visual and/or tactile indication that the seal component is in a second or upmost position with respect to the liner body and/or the at least one seal band. The distal capture system can thus indicate and guide the positioning of the seal component over a range of positions or a selected area on the liner body and/or the at least one seal band, making the seal component and the at least one seal easier to position.

BRIEF DESCRIPTION OF THE DRAWINGS

These and other features, aspects, and advantages of the present disclosure will become better understood regarding the following description, appended claims, and accompanying drawings.

FIG. 7 is an isometric view of an adjustable seal system according to another embodiment.

FIG. 8 is an isometric view of an adjustable seal system according to another embodiment.

FIG. 9 is an isometric view of an adjustable seal system according to another embodiment.

FIGS. 19-35 are partial views of the liner corresponding to FIG. 1 wherein alternative forms of seal rings are illustrated.

FIG. 39 is an isometric view of a seal system according to another embodiment.

FIG. 40 is a cross-section of the seal member of FIG. 39 according to an embodiment.

FIG. 41 is a cross-section of the seal member of FIG. 39 according to another embodiment.

DETAILED DESCRIPTION OF VARIOUS EMBODIMENTS

Figures 1, 2:
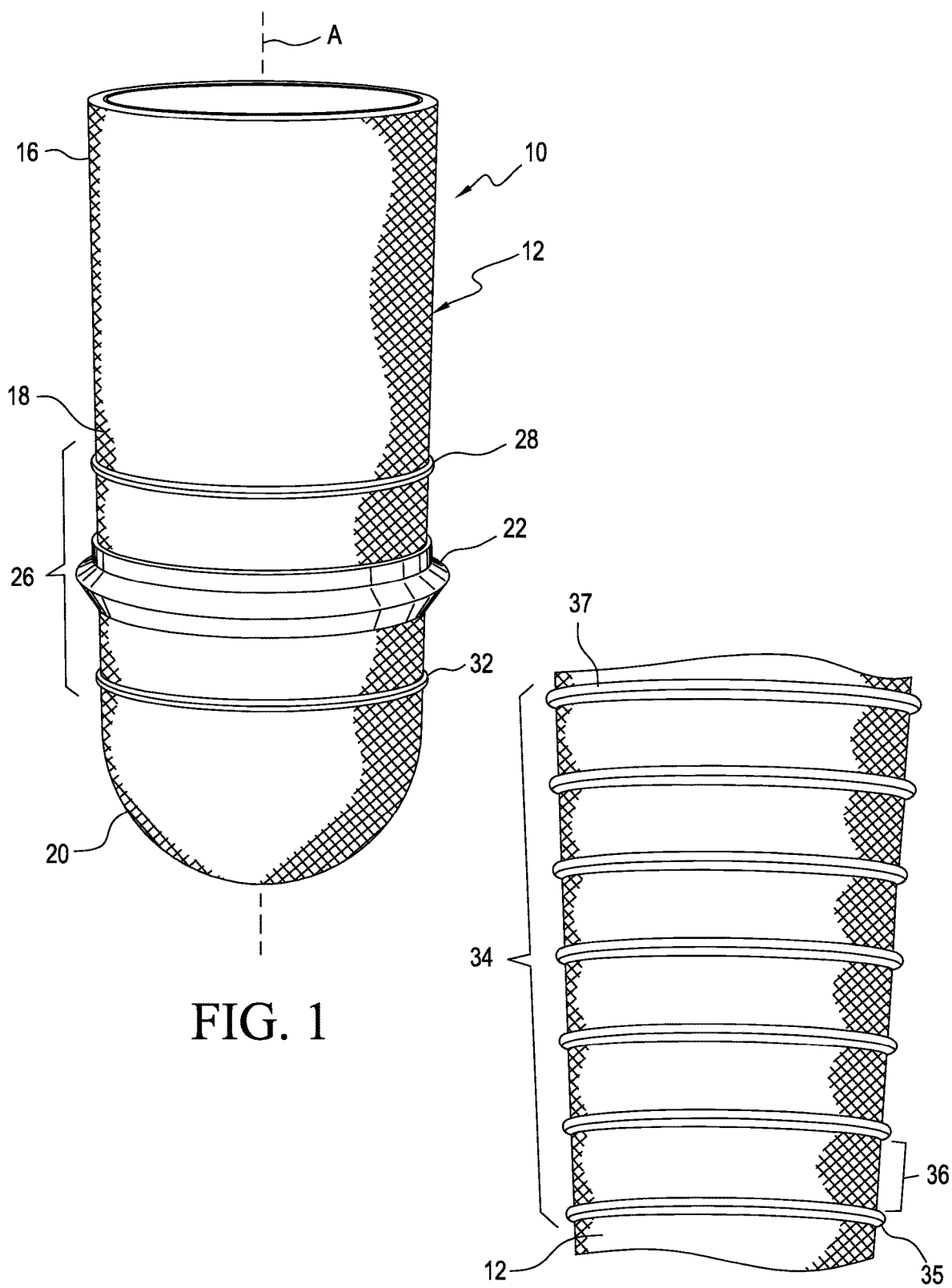
FIG. 1 is a perspective view showing an embodiment of a liner having a movable seal system.
FIG. 2 is a detailed view showing concentric seal bands disposed about an outer cover of the liner body.

A better understanding of different embodiments of the disclosure may be had from the following description read in conjunction with the accompanying drawings in which like reference characters refer to like elements.

In each of the embodiments discussed herein, the suspension liner is intended for use between a residual limb and a prosthesis, such as a hard socket, and to be air-tight when donned over a residual stump. The internal surface of the liner may be formed of a layer of silicone elastomer, therefore serving as a skin interface.

Silicone is advantageous in that it allows for different levels of softness and strength to be incorporated into the liners of the present application. Moreover, silicone permits the addition of selected supplements, such as petroleum jelly and aloe vera, which improve skin care and comfort. The suspension liner, however, can be constructed from a variety of other materials other than from silicone, and the embodiments herein are not limited to suspension liners formed from silicone.

An elasticity controlling matrix material may be provided on the exterior of the liner, the matrix material preferably being relatively compliant in a radial direction and substantially rigid or inelastic in an axial direction. The matrix material may extend over the distal or external side of the prosthesis, and is advantageous in that it prevents movement of the liner when a prosthesis is worn thereover.

A liner in accordance with this disclosure may be fabricated in a sufficient number of sizes to accommodate various sizes of residual limbs. In use, a liner of the type described herein is rolled up from the proximal to the distal end, placed over the distal end of the residual stump and rolled back up or "donned" over the stump like a stocking. This procedure and the benefits achieved thereby are described in detail in U.S. Pat. No. 4,923,474, granted on May 8, 1990 and incorporated herein by reference. In addition, any of the liners and sleeves mentioned herein may be constructed in the manner prescribed by U.S. Pat. No. 4,923,474.

The embodiments of the suspension liner of the present application may be constructed according to the molding methods described in U.S. Pat. No. 6,485,776, granted on Nov. 26, 2002 and the entirety of which is incorporated herein by reference.

As taught in U.S. Pat. No. 8,956,422, in use a liner carrying a seal component is worn on a residual limb and stepped into a prosthetic socket. As the residual limb is placed into the socket, the seal component forms an airtight seal with an interior surface of the socket and urges air out of the distal end of the socket through a distally positioned expulsion valve. When it is desired to release the connection between the liner and the socket, the valve is released, and the residual limb can be removed from the socket.

When sealing against a socket, it should be kept in mind that the vacuum is formed between the seal component and the distal end of the socket; no vacuum is created proximal of the socket between the liner and the socket. Depending on configurations of the seal component, the seal component may not completely press against the socket wall, in that only portions of the seal press against the socket wall. For example, seal rings of the seal component may press against the socket wall, but portions between the seal rings may not touch the socket wall.

Pressure is inversely proportional to the suspension force needed, so as to ensure stability and rotational control. The seal component preferably forms a hypobaric sealing membrane that conforms to the shape of the internal socket wall, providing an airtight seal between the suspension liner and the socket. It is often desirable that even pressure exists around the seal component in the connection between the socket and liner. There is preferably firm suspension among the liner, socket and residual limb.

In observing the suspension liner embodiment of FIG. 1, the liner 10 includes a liner body 12 defining an internal cavity for receiving a residual limb. The liner body 12 preferably has an elongate, generally conical shape, and defines a longitudinal axis A-A which extends between proximal and distal portions 16, 20. The proximal and distal portions 16, 20 are spaced apart by a middle portion 18. The liner body 12 may be formed from at least one material segment that is at least radially elastically extensible from a relaxed non-extended condition.

A seal component 22 is secured to an outer surface of the liner body 12 among at least one seal band 26 formed along the outer surface of the liner body 12. In this embodiment, the at least one seal band 26 defines a plurality of seal rings 28, 32 located about a circumference of the middle portion. The seal rings may be formed from a frictional material to maintain the seal component 22 on the liner 10. An example of a frictional material is silicone, however other suitable materials may be used.

The seal component 22 frictionally fits against at least one of the seal rings, and can be installed among any one of the seal rings, along the length of the liner body. The seal component 22 can likewise be removed from the liner body 12 and readjusted as considered necessary at a new location.

In this embodiment, the seal component is considered detachable in that it can be removed from the liner body, and adjustable so as to be reappointed on the liner body without any adhesive or permanency. According to a desired height of the seal component, the seal component can be installed among any one or more of the seal rings.

Various advantages are provided by this embodiment over known seal systems. The adjustable seal component can be placed proximally if desired to permit vacuum over the majority of the outer surface of the liner body to maximize suspension potential. The adjustable seal component can be arranged on the liner body outer surface to avoid sensitive areas, for example neuromas or scar tissue, to afford the user more comfort over systems where the seal component is at a fixed location.

The impact of volume fluctuations can be mitigated by placement of the seal component at an ideal location for a given user. For example, moving the seal component toward the proximal end of the liner body may compensate a decrease in volume. Further yet, donning and doffing of the liner is made easier. The liner may be inverted and rolled onto the residual limb without the seal component, and the seal component is only installed after the limb is donned on the residual limb.

The at least one seal band may take on a variety of configurations and is not limited to the configuration shown in FIG. 1. The at least one seal band may be circumferentially segment over the outer surface, and may take on a variety of thicknesses and shapes.

In an exemplary method of manufacturing the at least one seal band formed from silicone or other polymeric material on a textile-based outer surface or cover, the silicone seal band is formed so as to bleed or wet through the textile and interlock therewith.

Various types of materials may be used to form the at least one seal band. In the disclosed embodiments, a silicone is selected having low viscosity. The at least one seal band can form different patterns to reduce or eliminate any flow of silicone deposited onto the outer cover. Various yarn types may be selected as a basis in which silicone is encouraged or allows to wet or bleed through the textile, as well as certain weaves of the textile which facilitates wetting or bleeding of the material forming the at least one seal band.

In observing FIG. 2, a plurality of individual rings 34 extend about the circumference of the liner body. The rings 34 are spaced a distance 36 from one another at specific increments which may be uniform or non-uniform, such as with variable distances. The liner body 12 may also form protruding rings 35, 37 at distal and proximal ends delimiting the plurality of individual rings 34.

In an embodiment, the rings 34 can continuously spiral along the outer cover. This variation permits rings 34 having different widths and spacing, however each of the rings is continuously formed with another thereby continuously spiraling along the length of the outer cover. Of course, individual rings may be formed, such as in the embodiment of FIG. 2 having different widths, and spacing among one another without necessarily spiraling along the length of the liner body.

The at least one seal band of the embodiments may protrude outwardly from the outer cover at various depths, and embodiments may include a plurality of rings or ribs extending along the entirety of the liner body or only along certain segments. The profile of the at least one seal band may be configured to correspond to an interior portion of the seal component, for example the profile of the at least one seal band may form a profile mating a cavity along the interior surface of the seal component.

In addition to the at least one seal band, various patterns of a frictional material, such as silicone, can be deposited on the outer textile cover to achieve various benefits. One benefit includes rotational control, which is obtained by patterns of the frictional material on the outer cover to minimize rotational movement of the liner relative to the socket. As an additional benefit, a frictional material may serve to control or fine-tune characteristics of the liner. For example, the addition of silicone rings may serve to decrease radial and/or axial stretch by inhibiting the stretchability of the outer cover and liner body by being formed from a stiffer material. Alternatively, the rings may provide improved or additional cushioning for stabilizing soft tissue areas in some regions with wider, higher and/or more rings and patterns.

In another variation, the at least one seal band may be colored to provide guidance to the user as to a desirable position of the seal component. For example, if the silicone rings were colored or shaped differently from one another, a user may be able to discern where to locate the seal component. In yet another variation, a matting agent may be used to decrease the coefficient of friction of the at least one rib to improve donning and doffing of the liner. In yet another variation, the surface texture of the at least one seal band may be arranged so the coefficient of friction is adapted to ease donning and doffing of the liner on a user.

Figure 3:
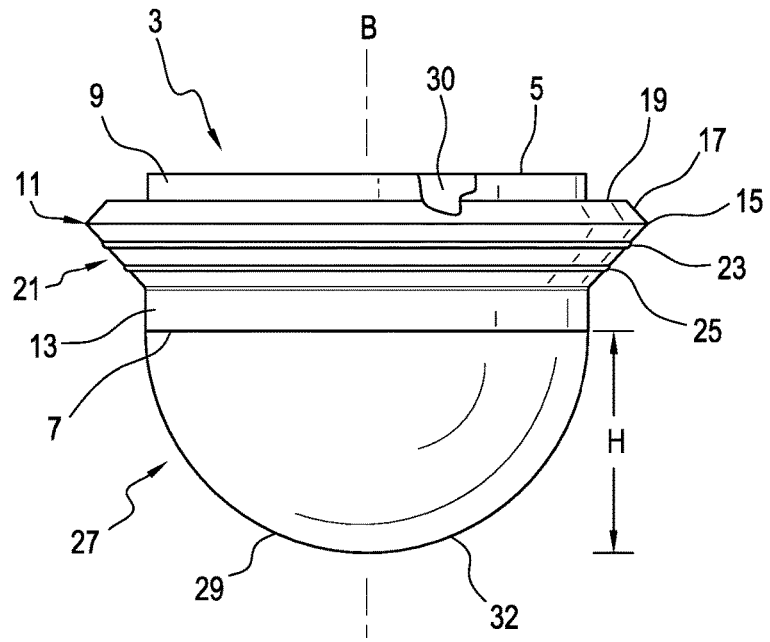
FIG. 3 is an isometric view of an adjustable seal system according to an embodiment.

FIG. 3 shows an adjustable seal system comprising a seal component 3 according to an embodiment. The seal component 3 is arranged to removably and securely engage the outer surface of a liner. The seal component 3 has an axis B-B and open upper and lower ends 5, 7 defining an opening extending therethrough and an inner surface 30 arranged to abut a surface of a liner body (e.g., liner body 12). For instance, the inner surface 30 can frictionally engage at least one of a plurality of seal bands on a liner and secure on the outer surface of the liner body.

The seal component 3 defines an upper portion 9 arranged for being flush against a liner body via the inner surface. A seal 11 is located below the upper portion 9 and above a lower portion 13. The seal 11 protrudes radially outward from the axis B-B relative to the upper portion 9. The seal 11 has a radially outermost portion or seal lip 15 arranged generally concentric with the upper portion 9.

The seal 11 has an upper segment 17 extending radially inwardly and upwardly from the seal lip 15 toward the upper portion 9. A clearance 19 is defined between the upper portion 9 and the upper segment 17 such that the seal 11 is arranged to be compressed against the upper portion 9. The seal 11 has a lower segment 21 extending outwardly from the lower portion 13 to the seal lip 15 and at least one radial seal 23, 25, and preferably at least two radial seals projecting outwardly from the lower segment 21.

The seal component 3 includes a distal capture system 27 at the lower end 7. The distal capture system 27 is arranged for creating a connection between the seal component 3 and a distal end of a liner after the liner is donned on a residual limb and the seal component is secured on an outer surface of a liner body. This advantageously assists a user with seal placement on a liner body, improving its ease of use.

The distal capture system 27 can have any suitable configuration but is shown including a distal cup member 29 having a closed bottom 32, preventing introduction of a liner body through the lower end 7, forcing a user to position the seal component 3 on a distal portion of a liner body via the upper end 5. This beneficially ensures correct orientation of the seal 11 by preventing the seal component 3 from being mistakenly inverted on the liner body.

As seen, the distal cup member 29 can define a height H and can be substantially rigid or inelastic in an axial direction. When the seal component 3 is installed onto a liner and the distal end of the liner engages the closed bottom 32 of the distal cup member 29, the distal capture system 27 can selectively fix the position of the seal 11 with respect to the liner body. The distal capture system 27 thus substantially controls the location of the seal 11 on the liner, helping to ensure proper positioning of the seal 11. This beneficially assists with seal placement for new or elderly users who may be unsure or unaware of proper seal placement, making the seal component easier to use. Further, the distal capture system 27 reduces the number of fine hand movements needed to locate and/or adjust the seal during use.

Optionally, the distal capture system 27 may be removable from the seal component 3, allowing the location of the seal 11 to be repositionable along the length of a liner body once the distal capture system 27 is removed.

It will be appreciated that the distal capture system 27 may be constructed from a variety of different materials and may be molded directly with the seal component or adhered, fastened or locked on the seal component. The distal capture system 27 may be permanently fixed or fixed only for the task of donning or doffing of the seal component. The distal capture system 27 may be formed differently from the seal component, and may be formed from a textile or different elastomer such as polyurethane.

Figure 4:
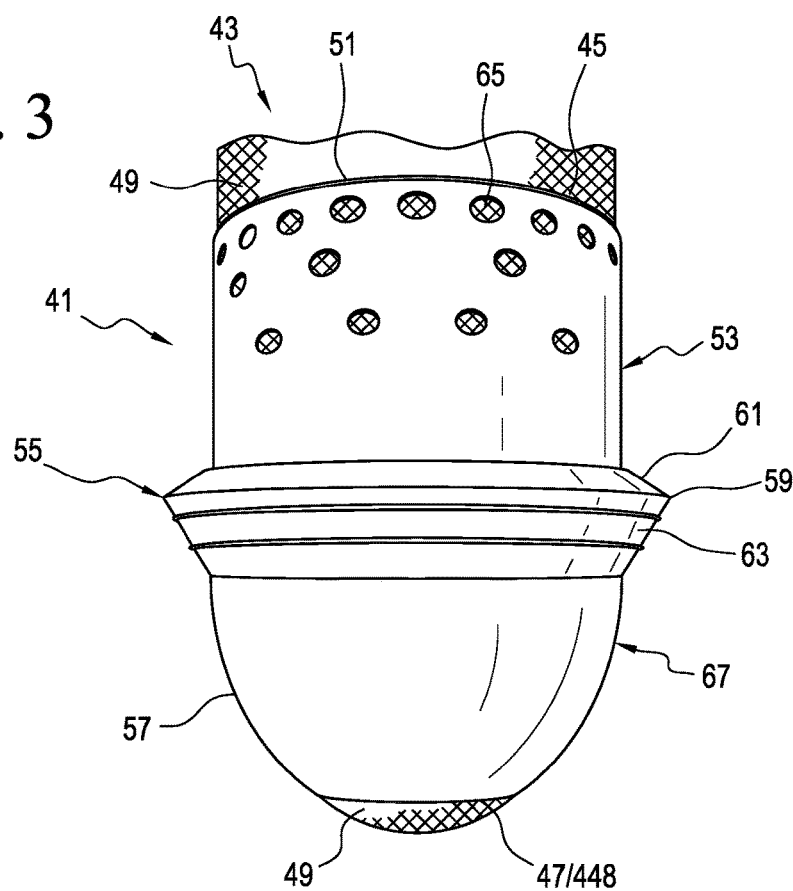
FIG. 4 is an isometric view of an adjustable seal system according to another embodiment.

FIG. 4 shows an adjustable seal system comprising a seal component 41 and a liner 43 according to another embodiment. The seal component 41 can include open upper and lower ends 45, 448 defining an opening extending therethrough and an inner surface arranged to abut a surface of a liner body 49 of the liner 43. For instance, the inner surface can frictionally engage at least one of a plurality of seal bands 51 on the liner body 49 and secure on the outer surface of the liner body 49.

The seal component 41 defines an upper portion 53 arranged for being flush against the liner body 49. The upper portion 53 can have a substantially uniform diameter along its height when positioned on the liner body 49 and an elongate configuration, increasing the interface between the seal component 41 and the liner body 49 when donned on the liner 43.

A seal 55 is located below the upper portion 51 and above a lower portion 57. The seal 55 protrudes radially outward from the upper portion 53. The seal 55 has a radially outermost portion or seal lip 59 arranged generally concentric with the upper portion 53. The seal 55 has an upper segment 61 extending radially inwardly and upwardly from the seal lip 59 toward the upper portion 53. The seal 55 has a lower segment 63 extending outwardly from the lower portion 57.

According to a variation, a plurality of perforations 65 are defined in the upper portion 53. When the seal component 41 is pulled over the distal end of the liner 43 after the liner 43 is donned on the residual limb, the perforations 65 can increase the stretchability of the upper portion 53.

In an embodiment, the seal component 41 includes a distal capture system 67 integral to the lower portion 57. As seen, the lower portion 57 includes a bottom edge defining a bottom opening 47. The lower portion 57 includes a curvature curving inwardly from the seal 55 toward the bottom opening 47. The diameter of the bottom opening 47 is arranged and dimensioned to prevent passage of the liner 43 through opening 47, which, in turn, causes the lower portion 57 to prevent further downward movement of the liner 43.

When the seal component 41 is pulled over the distal end of the liner 43 after the liner 43 is donned on the residual limb, the lower portion 57 can position the seal 55 in a fixed position with respect to the liner body 49. Thus, the distal capture system 67 can fix or set the location of the seal 55 on the liner, providing helpful seal placement assistance to a user. The opening 47 in the lower portion 55 can further provide improved proprioception with better linkage to the socket.

Figure 5:
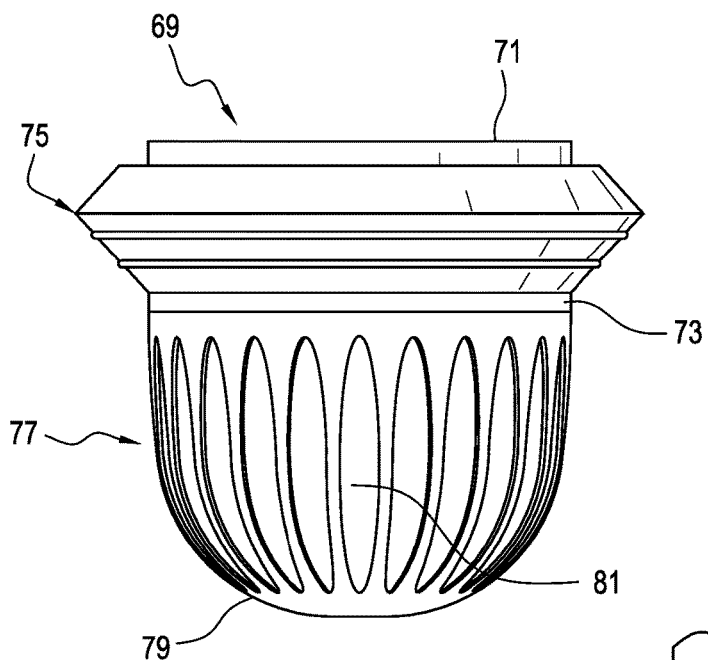
FIG. 5 is an isometric view of an adjustable seal system according to another embodiment.

FIG. 5 shows an adjustable seal system comprising a seal component 69 according to another embodiment. The seal component 69 can be similar to the seal component 3. For instance, the seal component 69 includes an upper portion 71, a lower portion 73, and a seal 75. The seal component 69 includes a distal capture system 77 for creating a connection between the seal component 69 and a distal end of a liner after the liner is donned on a residual limb and the seal component is secured on an outer surface of a liner body. This also can beneficially assist with seal placement on a liner body.

The distal capture system 77 comprises a distal cup member 79 similar to the distal cup member 29 except that it defines a plurality of longitudinal slots 81 distributed circumferentially about the distal cup member 79. The slots 81 can allow portions of a liner body to enter the slots 81, improving the connection between the seal component 69 and a liner. The slots 81 can also beneficially influence the axial and/or radial stiffness of the distal cup member 79 and provide improved proprioception.

Figure 6:
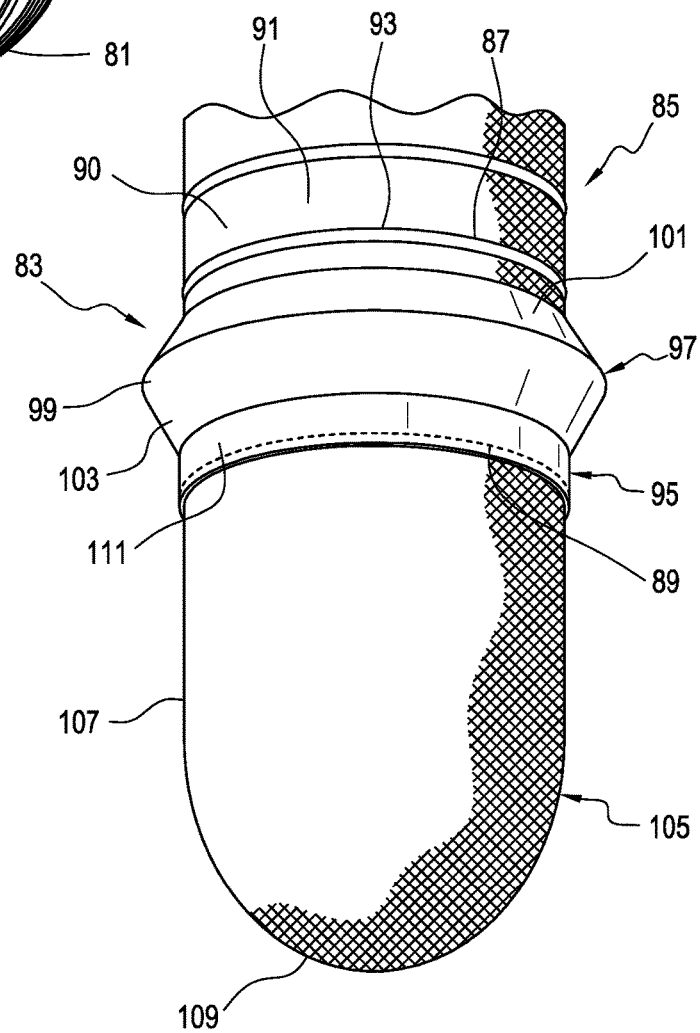
FIG. 6 is an isometric view of an adjustable seal system according to another embodiment.

FIG. 6 shows an adjustable seal system comprising a seal component 83 and a liner 85 according to another embodiment. The seal component 83 includes open upper and lower ends 87, 89 defining an opening extending therethrough and an inner surface arranged to abut an outer surface 90 of a liner body 91 of the liner 85. For instance, the inner surface can frictionally engage at least one of a plurality of seal bands 93 and secure on the outer surface 90 of the liner body 91.

The seal component 83 can define a lower portion 95 arranged for being flush against the liner body 91. The lower portion 95 has a substantially uniform diameter along its height when positioned on the liner body. A seal 97 is located above the lower portion 95 and protrudes radially outward from the lower portion 95. The seal 97 has a radially outermost portion or seal lip 99 arranged generally concentric with the lower portion 95. The seal 97 has an upper segment 101 extending radially inwardly and upwardly from the seal lip 99 toward the liner body 91. The seal 97 has a lower segment 103 extending outwardly from the lower portion 95.

A distal capture system 105 is attached at the lower end 89 of the seal component 83. Similar to the other distal capture systems, the distal capture system 105 is adapted to create a connection between the seal component 83 and a distal end of the liner 85 after the liner 85 is donned on a residual limb. This beneficially can control positioning of the seal component 83 on the liner body 91 and over at least one of the seal bands 93, making the seal component 83 easier to use and position.

In an embodiment, the distal capture system 105 can comprise a textile or a sock member 107 having an open upper end attached to the lower end 89 and a closed bottom end 109. The sock member 107 can be attached to the lower portion 95 in any suitable manner but is shown being attached via stitching 111.

The sock member 107 may include at least one material or textile section having an elasticity, which can be different from the seal component 83. The seal component 83 can be pulled over the distal end of the liner 85 until the distal end of the liner 85 engages the closed bottom end 109 of the sock member 107. In this position, the sock member 107 provides a reference point or visual indication that the seal component 83 is in a lower or lowermost position with respect to the liner body 91 and/or the seal bands 93.

The elastic configuration of the sock member 107 can allow for some stretching or movement of the seal component 83 away from the distal end of the liner 85 but such movement is limited as the sock member 107 becomes taut or reaches its elastic limit, thereby restricting and/or controlling upward movement of the seal component 83.

When the sock member 107 reaches its elastic limit, the sock member 107 provides a visual and/or tactile indication that the seal component 83 is in an upper or upmost position with respect to the liner body 91 and/or seal bands 93. The distal capture system 105 can thus indicate and control the positioning of the seal 11 over a range or selected area on the liner body 91 and/or seal bands 93, making the seal component 83 easier to position.

The elasticity of the sock member 107 can accommodate volume fluctuations of a residual limb by stretching and moving with the residual limb, improving user comfort. The textile material of the sock member 107 may be configured to reduce friction between the sock member 107 and the liner body 91, making the seal component 83 easier to don.

Optionally, the distal capture system 105 may be removable from the seal component 83, allowing the location of the seal 97 to be freely repositionable along the length of a liner body over different seal bands 93 once the distal capture system 105 is removed. According to a variation, the sock member 107 can include one or more sections having different elasticities.

FIG. 7 shows an adjustable seal system comprising a seal component 113 and a liner 115 according to another embodiment. Similar to the other embodiments, the seal component 113 has open upper and lower ends 117, 119, and an internal surface for securing over a liner body 121 of the liner 115. For example, the internal surface can engage and frictionally secure against at least one seal band 123 on the liner 115.

The seal component 113 has an upper portion 125 descending to a seal 127, and a lower portion 129 ascending to the seal 127. The seal 127 extends from the lower portion 129 and extends radially beyond the periphery of the upper portion 125. The upper portion 125 defines a recess 131 proximate the seal 127, and a bevel or edge 139 delimiting a top portion of the recess 131. The upper portion 125 has an elongate configuration, increasing the interface between the seal component 113 and the liner body 121.

The lower portion 129 defines a plurality of ribs 133, 135 circumferentially extending around the periphery of the lower portion 129. The ribs 133, 135 are arranged along the height of the lower portion 129 for improving sealing with a socket wall. The ribs may have the same or different cross-sectional shapes.

The seal 127 is arranged to protrude away from the liner 115 a distance when not installed in a socket, and subsequently collapse against the liner surface when placed and engaging a socket, essentially closing the distance. The seal 127 forms a flap 137 protruding away from the upper portion 125 a distance while having a base intersecting with the upper portion 125. The flap 137 generally has a size corresponding to the recess 131 such that upon insertion into a socket, the flap 137 is urged into the recess 131, and has an end portion that may abut the bevel 139.

The seal component 113 includes a distal capture system 141 at the lower end 119. The distal capture system 141 is adapted to create a connection between the seal component 113 and a distal end of the liner 115 after the liner 115 is donned on a residual limb and the seal component 113 is secured on the outer surface of a liner. This beneficially can control positioning of the seal component 113 on the liner body 121, making the seal component 113 easier to use.

In the illustrated embodiment, the distal capture system 141 can include a basket structure 151 comprising a base 143 and a plurality arms members 145 circumferentially distributed and spaced about a longitudinal axis of the basket structure 151. Open spaces or gaps 442 are defined between the arm members 145. The arm members 145 can extend in generally an axial direction between the base 143 and the lower end 119 of the seal component 113. The base 143 interconnects the arm arms 145 and can provide support to the distal end of a residual limb. The base 143 can have solid or supportive construction.

The base 143 and arm members 145 allow the basket structure 151 to provide both axial and radial support to a distal end of the liner 115 and residual limb. Moreover, the open spaces or gaps 442 formed between the arm members 145 offer improved proprioception with better linkage to a socket.

Each arm member 145 has an elongate configuration and includes a distal portion 147 extending from the base 143 and a proximal portion 149 attached to the lower end 119. The base 143 can interconnect the arm members 145. The system 141 can include four, six, eight, or any other suitable number of arm members 145.

According to a variation, the basket structure 151 can include at least one section formed of an elastomer or polymer, such as silicone, having an elasticity. The seal component 113 can be installed on the distal end of the liner 115 until the distal end of the liner 115 engages the base 143 of the basket structure 151. In this position, the basket structure 151 can provide a reference point or visual indication that the seal component 113 is in a first or lowermost position with respect to the liner body 121 and/or at least one seal band 123. In an embodiment, the basket structure 151 can be under relatively low tension in the lowermost position.

The elasticity of the basket structure 151 can allow for some upward or proximal movement of the seal component 113 away from the distal end of the liner 115 but such movement is limited as the basket structure 151 becomes taut or reaches its elastic limit, thereby restricting and/or controlling upward movement of the seal component 113.

When the basket structure 151 reaches its elastic limit, the basket structure 151 provides a visual and/or tactile indication that the seal component 113 is in second position or upmost position with respect to the liner body 121 and/or the seal bands 123. The distal capture system 141 can thus indicate and guide the positioning of the seal component 123 over a range of positions or selected area on the liner body 121 and/or seal bands 123, making the seal component 113 and the seal easier to position.

The spacing of the arm members and elasticity of the basket structure 151 can accommodate volume fluctuations of a residual limb by stretching and moving with the residual limb, improving user comfort. The basket structure 151 can also be formed of a material having a compressible configuration, improving user comfort.

The basket structure 151 beneficially provides a relatively thin and/or minimalist construction, providing improved proprioception with better linkage to a socket. Such a minimalist construction can further reduce pressure felt by the user at the distal end of the liner.

FIG. 8 shows an adjustable seal system comprising a seal component 153 and a liner 155 according to another embodiment. The seal component 153 is similar to the seal component 113. For instance, it has open upper and lower ends 157, 159, and an internal surface for securing over a liner body 161 of the liner 155. In an embodiment, the inner surface can engage and frictionally secure against at least one seal band 163 on the liner 155. The seal component 153 has an upper portion 165 descending to a seal 167, and a lower portion 169 ascending to the seal 167.

The seal component 153 includes a distal capture system 171 at the lower end 159. The distal capture system 171 can be similar to the distal capture system 141, including a basket structure 181 comprising a base 173 and a plurality of arm members 175 circumferentially distributed and spaced about a longitudinal axis of the basket structure 181. The basket structure 181 can be made from any suitable material but is illustrated made of silicone.

As seen, the basket structure 181 further includes a plurality of linking supports 177 distributed above the base 173, and extending between the arm members 175. The linking supports 177 according to a variation can comprise ribs 177 forming concentric rings distributed along a height of the basket structure 181, with the upper ribs defining a larger diameter than the lower support ribs.

The linking supports 177 advantageously reinforce the arm members 175 in an axial direction, helping the basket structure 181 axially support the distal end of the liner when the seal component 153 is pulled onto the liner 155. They can further reinforce the arm members 175 against radially outward forces, helping to secure the seal component 152 on the liner body 161.

FIG. 9 shows an adjustable seal system comprising a seal component 183 and a liner 185 according to another embodiment. The seal component 183 is similar to the seal component 153 except that it includes a distal capture system 187 comprising a basket structure 189 formed with one or more laces 191. The one or more laces 191 can be laced through and attached to the seal component 183. For instance, the one or more laces 191 can include a plurality of laces intersecting one another at the distal end of a liner body 193. Each lace 191 can include a pair of free ends attached to a lower end 193 of the seal component, with a resulting loop intersecting the other laces at the distal end of the basket structure 189. The laces 191 can be formed of any suitable material. For instance, the laces 191 can be formed of an axial stiff material.

The seal component 183 can be installed on the distal end of the liner 185 until the distal end of the liner 185 engages the distal end of the basket structure 187. Because the laces are axially stiff, they can restrict further upward movement of the seal component 183. The basket structure 189 can thus fix or indicate the location of the seal on the liner 185, assisting with seal placement on the liner body 193. This advantageously positions the seal for new and/or elderly users who may be unsure about the proper placement of the seal between the liner 185 and a socket.

Figure 10:
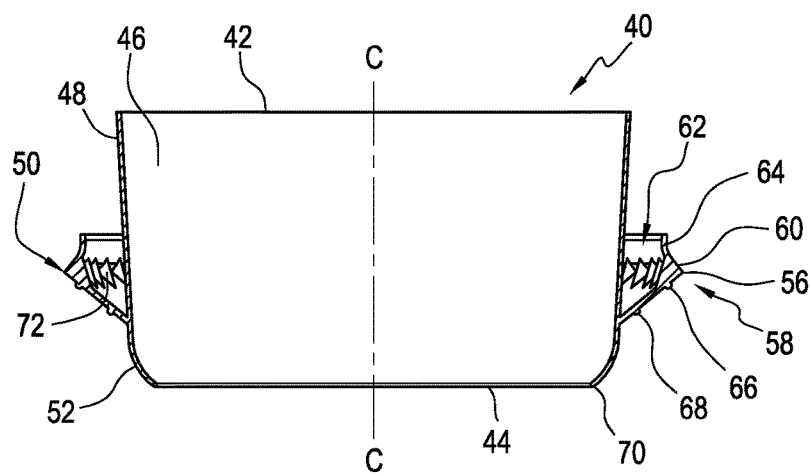
FIG. 10 is a cross-section of an adjustable seal system according to an embodiment.

FIG. 10 shows a cross section of an adjustable seal system comprising a seal component 40 according to another embodiment. The seal component 40 has an axis C-C and open upper and lower ends 42, 44 defining an opening extending therethrough and an internal surface 46 arranged to abut a surface of a liner body. The inner surface 46 can frictionally engage at least one of a plurality of seal bands on a liner and secure on the outer surface of the liner body.

The seal component 40 defines an upper portion 48 arranged for being flush against a liner body via the inner surface 46. A seal 50 is located below the upper portion 48 and above a lower portion 52, and generally at a middle portion 54. The seal 50 protrudes radially outward from the axis C-C relative to the upper portion 48. The seal 50 has a radially outermost portion or seal lip 56 arranged generally concentric with the upper portion 48.

The seal 50 has an upper segment 60 extending radially inwardly from the seal lip 56 toward the upper portion 48. A clearance 62 is defined between the upper portion 48 and the upper segment 60 such that the seal 50 is arranged to be compressed against the upper portion 48. The seal 50 defines a flap 64 extending from the upper segment 60, and spaced from the upper portion 48 by the clearance 62.

The upper segment 60 and flap 64 of the seal 50 have a curvilinear or arcuate configuration such that the width of the clearance 62 is variable. For instance, the upper segment 60 and the flap 64 have a curvature descending to the seal lip 56. The form of the upper segment and flap advantageously decreases the likelihood of the seal 50 undesirably sticking to or flattening out against the upper and/or middle portions 48, 54 of the seal component 40 when the seal component is inserted into a socket. It also provides an increased sealing force between the seal component 40 and a socket.

The seal 50 has a lower segment 58 extending outwardly from the lower portion 52 to the seal lip 56 and at least one radial seal 66, 68, and preferably at least two radial seals, projecting outwardly from the lower segment 58.

The lower portion 52 defines a bottom edge with a curvature 70 and the upper portion 48 can have a substantially uniform diameter along its height. The lower portion 52 may have a decreasing diameter toward the lower end 42, and is arranged to be compressed against the liner when the seal component 40 is donned thereon. The curvature of the bottom edge may be undersized to minimize movement of the seal component 40 when donning the socket.

The seal component 40 may include interior blades 72 located along the interior surface of the seal 50. The interior blades 72 can be arranged obliquely to the axis C-C, and arranged to collapse against a liner exterior wall. The blades 72 may beneficially reinforce the seal 50 to provide a stronger interface between the interior socket wall and the liner. The blades 72 can also increase the interface between the interior portion of the seal 50 against the liner when collapsed in a socket.

The blades 72 can compensate for volume changes in the residual limb by expanding and exerting pressure against an interior surface of the socket so as to improve suspension of the liner over known suspension liners with seals.

The blades 72 can be arranged obliquely to the axis C-C, permitting the blades to expand outwardly as the liner is donned onto the residual limb and fold down toward the seal wall with the possibility of some overlap over each of the blades as the liner is doffed. The blades 72 are at an angle so as to ensure that each blade folds in a proper predetermined direction so as to avoid the creation of pressure points. The blades 72 are not limited to an obliquely extending configuration but may be arranged in any number of configurations such as either generally parallel or perpendicular relative to a longitudinal axis of the liner.

Figure 11:
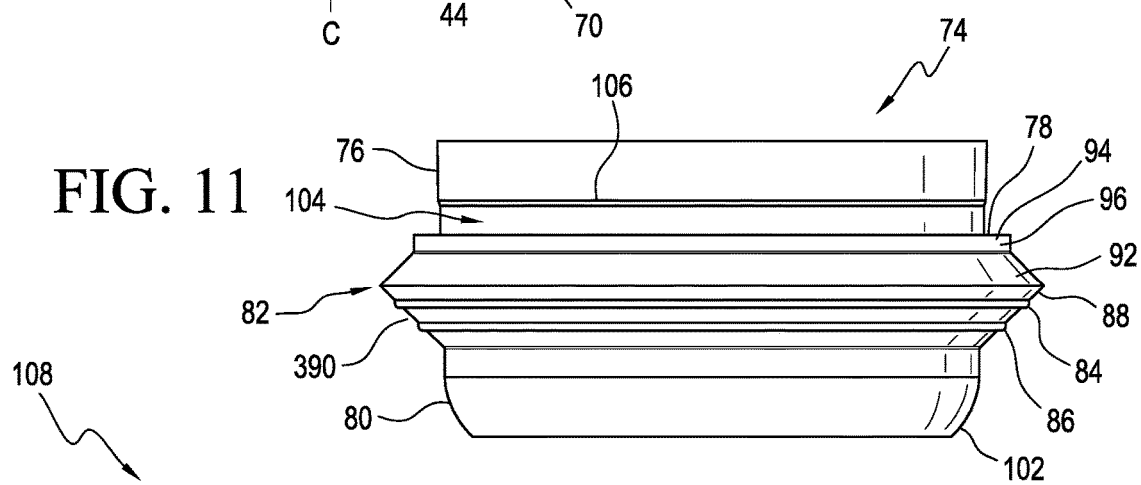
FIG. 11 is an isometric view of an adjustable seal system according to another embodiment.

FIG. 11 shows yet another embodiment of an adjustable seal system comprising a seal component 74. The seal component 74 defines an opening extending therethrough and an internal surface arranged to abut a surface of a liner body. The seal component 74 includes upper, middle, and lower portions 76, 78, 80, respectively, with a seal 82 located near or at the middle portion 78. Optionally, the seal component 74 includes interior blades, arranged in the same manner as in the seal component 40. The seal component 74 defines radial seals 84, 86 located below the seal 82, and generally within the lower portion 80.

The seal 82 has a radially outermost portion of seal lip 88 arranged generally concentric with the upper portion 76. The seal 82 has a lower segment 390 extending outwardly from the lower portion 80 to the seal lip 88. The seal 82 has an upper segment 92 extending inwardly from the seal lip 88 toward the upper portion 76. A clearance 94 is defined between the upper portion 76 and the upper segment 92 such that the seal 82 is arranged to be compressed against the upper portion 76.

The upper segment 92 is angled relative to the upper portion 76. A flap 96 extends from the upper segment 92, and arranged generally upright and/or parallel with the upper portion 76. The flap 96 is spaced from the upper portion 76 by the clearance 94. The lower portion 80 defines a bottom edge with a curvature 102 and the upper portion 76 has a substantially uniform diameter along its height.

The upper portion 76 defines a circumferential recess 104 proximate the seal 82, and a shoulder 106 delimiting a top portion of the recess 104. The upper segment 92 and/or the flap 96 generally has a size corresponding to the recess 104 such that upon insertion into a socket, the flap 96 is urged into the recess 104, and has an end portion that may abut the shoulder 106. This can force the upper segment 92 and/or the seal lip 88 further away from the upper portion 76, beneficially decreasing the likelihood of the seal 82 undesirably sticking to or flattening out against the upper and/or middle portions 76, 78 of the seal component 74. It can also increase the sealing force between a socket wall and the seal, providing improved suspension. In addition, it can reduce the overall thickness of the seal component 74, providing a more streamlined seal profile.

Figure 12:
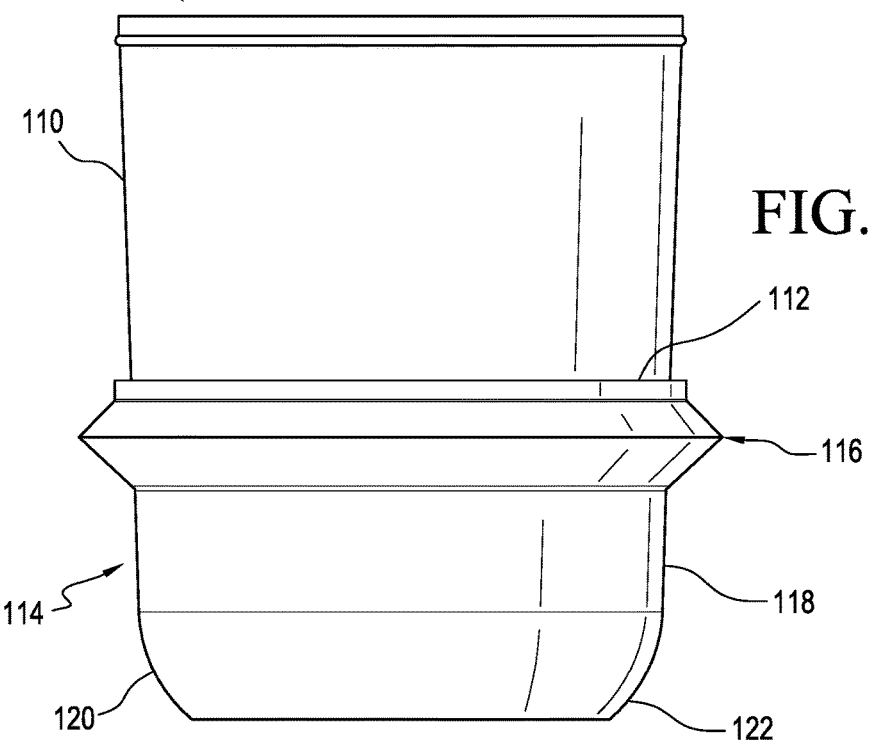
FIG. 12 is an isometric view of an adjustable seal system according to another embodiment.

FIG. 12 shows yet another embodiment of an adjustable seal system comprising a seal component 108. The seal component 108 includes upper, middle, and lower portions 110, 112, 114, respectively, with a seal 116 located at or near the middle portion 112.

The upper portion 110 has a substantially uniform diameter along its height and an elongate configuration, increasing the interface between the upper portion 110 and the liner body when donned on the liner.

The lower portion 114 has an upper section 118 with a substantially uniform diameter and a lower section 120. The lower section 120 defines a bottom edge with a curvature 122. The lower section 120 can have a decreasing diameter toward the bottom edge, and is arranged to be compressed against the liner when the seal component 108 is donned thereon. The curvature 122 of the bottom edge may be undersized to minimize movement of the seal component 108 when donning the socket.

Figure 13:
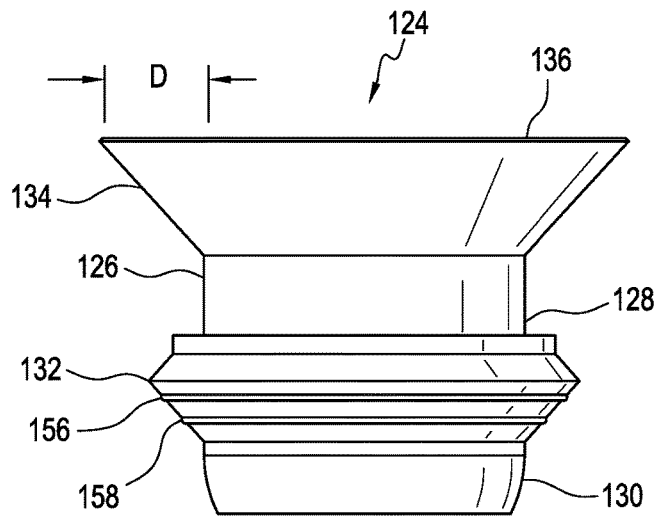
FIG. 13 is an isometric view of an adjustable seal system according to another embodiment.

FIG. 13 shows yet another embodiment of an adjustable seal system comprising a seal component 124. The seal component 124 defines an opening extending therethrough and an internal surface arranged to abut a surface of a liner body. The seal component 124 includes upper, middle, and lower portions 126, 128, 130, respectively, with a seal 132 located near or at the middle portion 128. The seal component 124 defines radial seals 156, 158 located below the seal 132, and generally within the lower portion 130.

As shown, a proximal part 134 extends upwardly and outwardly from the upper portion 126. The proximal part 134 has a conical configuration with an increasing diameter toward an upper end 136. The proximal part 134 is arranged to protrude away from a liner surface a distance D when not installed in a socket, and subsequently collapse against the liner surface when placed and engaging a socket, essentially losing the distance D.

The diameter of the upper end 136 is oversized relative to a liner, facilitating positioning of the seal component 124 on the liner body. For instance, the larger upper diameter of the proximal part 134 may make it easier for an elderly user to insert its residual limb into the opening of the seal component 124.

Moreover, the proximal part 134 can better accommodate a wider range of sizes and shapes of a residual limb. The proximal part 134 can also provide a handle that the user can grasp to pull the seal component 124 onto the liner body against any resistance by the liner body and an interior surface of the seal component. The proximal part 134 may be constructed from a variety of different materials and may be molded directly with the seal component 124.

Figure 14:
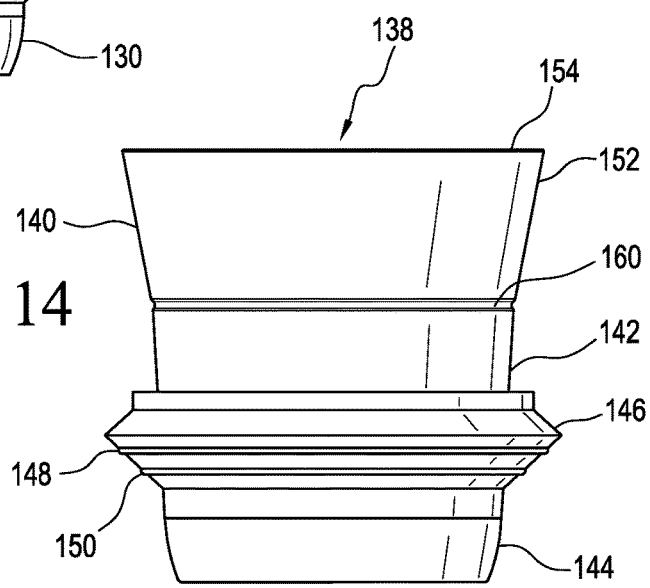
FIG. 14 is an isometric view of an adjustable seal system according to another embodiment.

FIG. 14 shows yet another embodiment of an adjustable seal system comprising a seal component 138. The seal component 138 defines an opening extending therethrough and an internal surface arranged to abut a surface of a liner body. The seal component 138 includes upper, middle, and lower portions 140, 142, 144, respectively, with a seal 146 located near or at the middle portion 142. The seal component 138 defines radial seals 148, 150 located below the seal 146, and generally within the lower portion 144.

A proximal part 152 extends upwardly and outwardly from the upper portion 140. Like the proximal part 134, the proximal part 152 has a conical configuration with an increasing diameter toward an upper end 154. The proximal part 152 may exhibit less of a taper than the proximal part 134.

The proximal part 152 may be adhered, fastened, or attached to the upper portion 140. The proximal part 152 may be formed differently from the seal component, and may be formed from the same material as the upper portion 140, a textile, or different elastomeric such as polyurethane.

The connection between the proximal part 152 and the upper portion 140 can define a folding structure. Due to the flexibility of the proximal part 152, the proximal part 152 may fold along a fold line 160 and onto a liner body when donning the socket.

Figure 15:
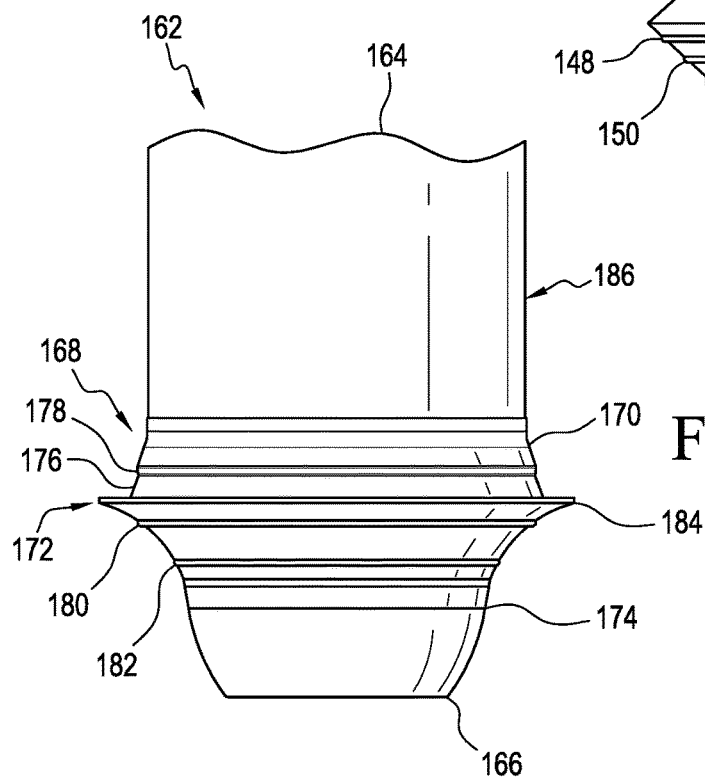
FIG. 15 is an isometric view of an adjustable seal system according to another embodiment.

FIG. 15 shows yet another embodiment of an adjustable seal system comprising a seal component 162. The seal component 162 has open upper and lower ends 164, 166, and an internal surface for securing over a liner. For instance, the internal surface can be arranged to engage and frictionally secure against at least one seal band on a liner.

The seal component 162 has an upper portion 168 with a curvature 170 descending to a seal 172, and a lower portion 174 curvingly ascending to the seal 172. The seal 172 extends from the lower portion 174 and extends a distance beyond the periphery of the curvature 170. The upper portion 168 defines a recess 176 formed by the periphery of the curvature 170 proximate the seal 172, and a bevel 178 delimiting a top portion of the recess 176 from the curvature 170.

The lower portion 174 has a generally bell-shaped curvature and defines a plurality of ribs 180, 182 circumferentially extending around the periphery of the lower portion 174. The ribs are arranged along the height of the lower portion 174 to improve sealing with a socket wall. The ribs may have different cross-sectional shapes.

The seal 172 is arranged to protrude away from a liner surface a distance when not installed in a socket, and subsequently collapse against the liner surface when placed and engaging a socket, essentially losing the distance.

The seal 172 forms a flap 184 protruding away from the upper portion 168 a distance while having a base intersecting with the upper curvature 170. The flap 184 generally has a size corresponding to the recess 176 such that upon insertion into a socket, the flap 184 is urged into the recess 176, and has an end portion that may abut the bevel 178.

A proximal part 186 extends upwardly from the upper portion 168 to the upper end 164. The proximal part 186 has a substantially uniform diameter along its height and an elongate configuration, increasing the interface between the seal component 162 and the liner body when donned on the liner.

The proximal part 186 may be adhered, fastened, or attached to the upper portion 168. The proximal part 186 may be formed differently from the seal component 162, and may be formed from a different elastomeric such as polyurethane.

Figure 16:
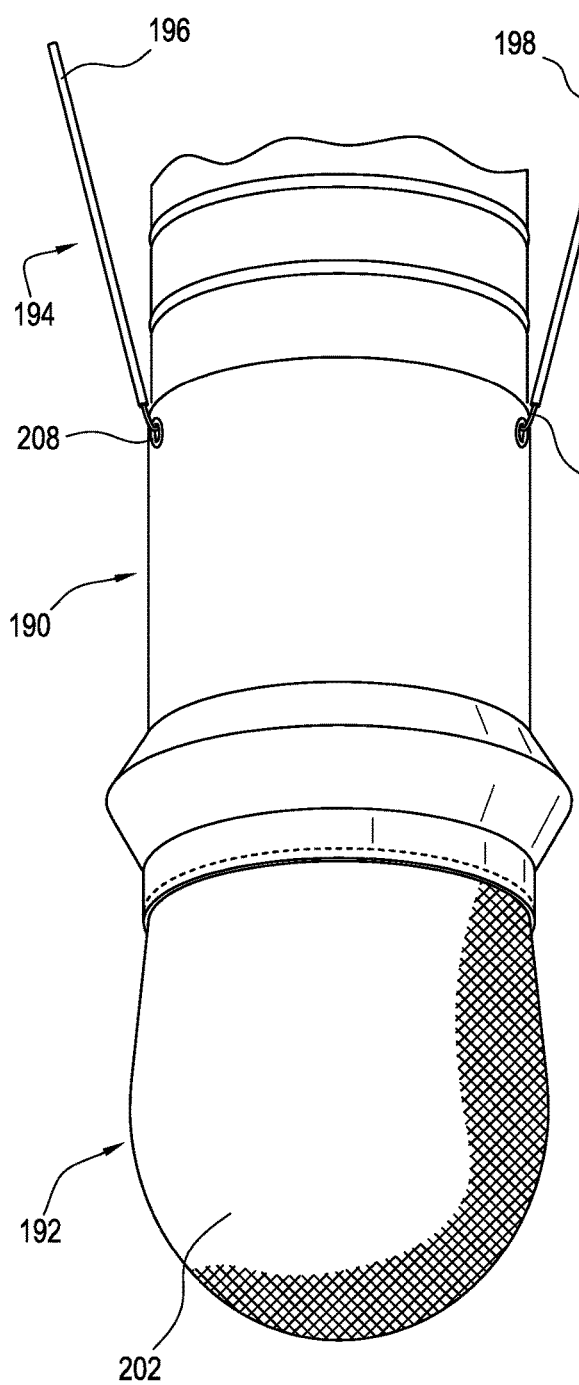
FIG. 16 is an isometric view of an adjustable seal system according to another embodiment.

FIG. 16 shows another embodiment of an adjustable seal system comprising a seal component 190 and a liner 192. It will be appreciated that the seal component 190 can be or similar to any embodiment of the seal components disclosed herein. For instance, the seal component 190 can be repositionable along a height of a liner body 202 of the liner 192, and arranged to create a seal between the liner 192 and a socket.

The adjustable seal system can include a separate handle system 194 having opposed handles 196, 198 that a user can grasp to pull the seal component 190 onto the liner body 202 against any resistance by the liner body 202 and an interior surface of the seal component 190.

The handle system 194 can be an add-on module and/or removable from the seal component 190 after donning the seal component 190 on the liner body 202. For instance, the distal end portions of the handles 196, 198 can each define a first mounting portion arranged to selectively mate with a corresponding mounting portion on the seal component 190. In an embodiment, the mounting portion on the handle can comprise a hook member 206 and the mounting portion on the seal component 190 can be an eyelet 208 including a grommet. In other embodiments, the mounting portion can comprise a first magnetic member and the mounting portion on the seal component 190 can be a second magnetic member.

In use, a user can mount the handles on the seal component 190 via the mounting portions. The user can then grasp the handles 196, 198 to pull to seal component 190 onto the liner body 202 positioned on a residual limb. When the seal component 190 is in a satisfactory position, the user can disconnect the handles 196, 198 from the seal component 190 and insert the liner 192 and seal component 190 in a socket. This advantageously facilitates placement of the seal component 190 on the liner body 202.

Figure 17:
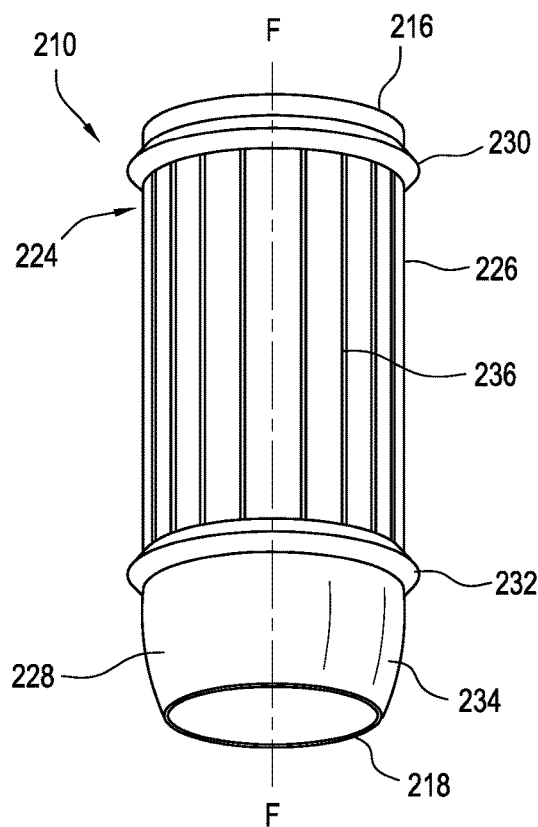
FIG. 17 is an isometric view of an adjustable seal system according to another embodiment.
Figure 18:
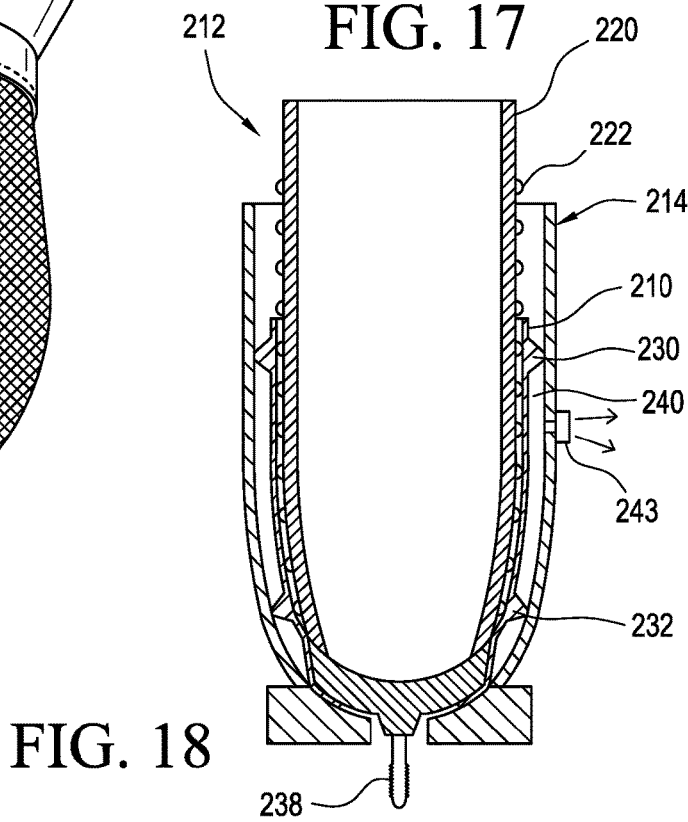
FIG. 18 is a cross-section of the seal system of FIG. 17.

FIGS. 17 and 18 show another embodiment of an adjustable seal system comprising a seal component 210, a liner 212, and a socket 214. The seal component 210 defines an axis F-F, and open upper and lower ends 216, 218 defining an opening extending therethrough and an internal surface arranged to abut a surface of a liner body 220. For instance, the inner surface can frictionally engage at least one of a plurality of seal bands 222 on the liner 212 and secure on the outer surface of the liner body 220. The liner body 220 may be formed of an elastomer and may or may not include a fabric cover.

The liner 212 can be a locking type liner. For instance, a locking pin 238 can be secured to a distal end of the liner 212. The pin 238 may be mounted to the liner 212 by being molded or screwed into a distal end of the liner 212. The pin is arranged to engage a locking assembly that may or may not be laminated into the socket 214. The locking assembly is arranged to be connected to the components connecting to a prosthetic device (e.g., prosthetic foot) and effectively couples the liner 212, the socket 214, and the components together.

The seal component 210 defines an upper portion 224, a middle portion 226 having an elongate configuration, and a lower portion 228. An upper seal 230 is located above the middle portion 226, and generally at the upper portion 224. A lower seal 232 is located below the middle portion 226, and generally at the lower portion 228.

The lower portion 228 defines a bottom edge with a curvature 234 with a decreasing diameter toward the lower end 218, and is arranged to be compressed against the liner body 220 when the seal component 210 is donned thereon. The curvature of the bottom edge may be undersized to minimize movement of the seal component 210 when donning the socket 214.

The middle portion 226 can define a plurality of perforations or channels 236 distributed circumferentially about the axis F-F and extending in a generally longitudinal direction between the upper and lower seals 230, 232. In an embodiment, the channels 236 can extend completely through the thickness of the middle portion 226, beneficially allowing the expulsion of air from the outer surface of the liner 210 through the channels 236 and between the upper and lower seals 230, 232 as described in more detail below. The seal component 210 can be repositionable along a height of the liner body 220, and arranged to create a seal between the liner 212 and the socket 214.

In use, the liner 212 is installed on a residual limb and the seal component 210 is installed on the liner body 220, frictionally engaging at least one of the seal bands 222. The residual limb and liner 212 with the seal component 210 are then inserted in the socket 214.

With the liner 212 inserted in the socket 214, the locking pin 238 can extend through an axial opening in the distal end of the socket 214 for securing the socket 214 and liner 212 relative to a prosthetic device, providing locking suspension.

As seen in FIG. 17, the upper seal 230 and the lower seal 232 can engage the inner wall of the socket 214, defining a vacuum region 240 between the upper and lower seals 230, 232, the inner wall of the socket 214, and middle portion 226 of the seal component 210. Upon application of a pulling force on the liner 212 relative to the socket 214, suction is created in the vacuum region 240 tending to retain the liner 212 within the socket 214. In the illustrated embodiment, a valve 243 attached to the socket wall is in fluid communication with the vacuum region 240. The valve 243 can be arranged to allow for the expulsion of air from the vacuum region 240, and to isolate the vacuum region 240 from atmosphere after the liner 212 with the residual limb has been fully inserted within the socket 214.

Optionally, to more positively secure the liner 212 within the socket 214, a vacuum pump can be fluidly attached to the valve 243 and used to evacuate the vacuum region 240. The valve 243 or other appropriate device can be used to open and close the vacuum region 240 to surrounding atmosphere. The vacuum pump can be directly attached to the valve 243 and/or indirectly attached to the valve 243.

This system of this embodiment secures the liner 212 in the socket 214 using both seal-in suspension and locking suspension, beneficially reducing the likelihood of pistoning of the liner 212 within the socket 14. Further, the seal-in suspension can stabilize volume of the residual limb and control pistoning while the locking pin 238 provides secondary suspension. Moreover, because the vacuum region 240 is fluidly isolated from the locking pin, the locking pin beneficially does not need to be sealed.

As described above, the inner surface of embodiments of the seal component can engage at least one of a plurality of seal bands to secure the seal component on the outer surface of a liner body. It will be appreciated that the liner may include an outer textile cover or may not include an outer textile covering. The seal bands may protrude radially outwardly from the outer cover or outer surface of the liner body at various depths.

FIGS. 19-35 illustrate alternative embodiments of the seal bands. As shown in FIGS. 19 and 20, a liner body 242 can include a proximal portion 245, a distal portion 247, and a plurality of seal bands 244 located along a length of the liner body 242 between the proximal and distal portions 245, 247 and on the outer surface of the liner body 242. The seal bands 244 can be located along a length of the proximal portion 245, the distal portion 247, or both the proximal portion 245 and the distal portion 247.

The seal bands 244 can include individual generally horizontal rings 246 extending about a circumference of the liner body 242. The rings 246 can be spaced a distance D1 from one another at specific increments which may be uniform or non-uniform, such as with variable distances.

When a seal component is installed on the liner body, the seal rings 246 can define a sealing surface between the seal component and the liner body 242 to maintain the seal component on the liner body. The seal rings 246 are shown as being generally horizontal however it will be appreciated that one or more complete rings extending in different orientations about the circumference of the liner body 242 can also create the sealing surface.

FIG. 21 offers a variation of a plurality of rings 248 continuously spiraling along the outer surface of the liner body 242. The rings 248 can include a first ring 248A spiraling in a first direction and a second ring 248B spiraling in a second direction such that the first and second rings 248A, 248B intersect one another at various points 248C along the length of the liner body 242. This variation permits rings 248 to have different widths and spacing, however each of the rings is continuously formed with another thereby continuously spiraling along the height of the liner body 242. Of course, individual rings may be formed having different widths, and spacing among one another without necessarily spiraling along the length of the liner body 242.

FIGS. 22-24 offer another variation of a plurality of individual rings 250 extending obliquely about the circumference of the liner body 242 between the distal portion 247 and the proximal portion 245. The rings 250 are spaced a distance D2 from one another at specific increments which may be uniform or non-uniform, such as with variable distances. As seen in FIG. 24, the rings 250 may be more closely spaced near or at the proximal portion 245 than at the distal portion 247, helping to stabilize soft tissue and/or provide cushioning. In other embodiments a second plurality of individual rings can extend obliquely about the circumference of the liner body 242 in a different orientation so as to from a cross-hatch type pattern.

In some variations, the seal bands are arranged to influence the interaction between the liner body 242 and a socket, and/or characteristics of the liner. For instance, when the seal component is installed on the liner body 242, some of the seal bands may be located outside (e.g., proximally and/or distally) the seal component. These seal bands outside the seal component can increase a coefficient of friction between the liner body 242 and a socket, which, in turn, can help limit unwanted rotational and/or axial movement between the liner body 242 and the socket.

In other embodiments, the materials, durometer, stretchability, additives and/or surface finish of the seal bands may be controlled or selected to influence the interaction between the liner body 242 and a socket. For instance, one or more of the seal bands can include magnetic particles and the socket can include one or more ferromagnetic materials (e.g., steel, iron, cobalt, or other suitable metal) to create a magnetic connection between the liner body 242 and the socket when the liner is inserted in the socket. In yet another variation, a matting agent may be used to decrease the coefficient of friction of at least one of the seal bands to improve donning and doffing of the liner. In yet other variations, the surface texture of at least one seal band may be arranged so that the coefficient of friction is adapted to ease donning and doffing of the liner on a user. Alternatively, the rings may provide improved or additional cushioning for stabilizing soft tissue areas in some regions with wider, higher and/or more rings and patterns.

Figure 25:
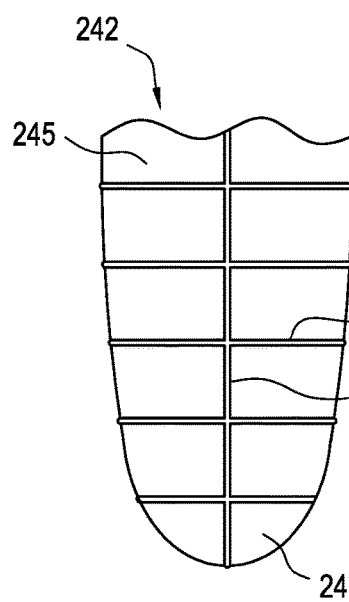

FIG. 25 offers another variation of the seal bands. A plurality of individual seal rings 252 extend radially or horizontally about the circumference of the liner body 242. The seal rings 252 define a sealing surface between a seal component and the liner body 242 when the seal component is installed on the liner body 242. The seal rings 252 may also serve to decrease radial stretch by inhibiting the stretchability of the liner body 242 and outer cover by being formed from a stiffer material. Further, the seal rings 252 outside the seal component can increase the coefficient of friction between the liner body 242 and a socket to reduce the likelihood of rotational movement between the liner body 242 and the socket.

At least one seal band 254 is shown extending in a general axial or vertical direction between the proximal and distal portions 245, 247, traversing the seal rings 252 and forming a grid-like pattern. This is beneficial because portions of the at least one seal band 254 outside the seal component can increase the coefficient of friction between the liner body 242 and the socket, improving suspension. In addition, the at least one seal band 254 may serve to decrease axial stretch of the liner body 242 by inhibiting the stretchability of the liner body 242 and/or the outer cover by being formed from a stiffer material.

Figure 26:
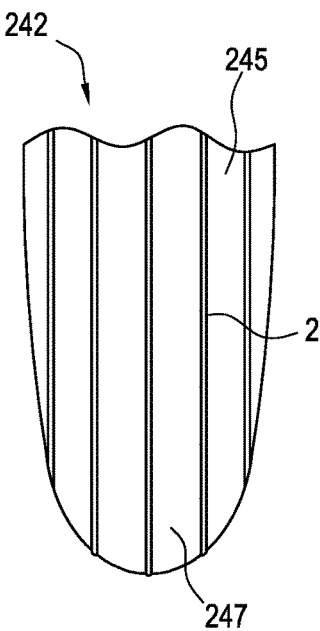

FIG. 26 offers another variation of a plurality of seal bands 256 extending in a general axial direction between the proximal and distal portions 245, 247 and distributed circumferentially about the liner body 242. Each seal band 256 may extend along a length of the liner body 242. The seal bands 256 may extend completely between proximal and distal ends of the liner body 242 or along only a partial length of the liner body 242. The axial orientation of the seal bands 256 is advantageous because the seal bands 256 can decrease the axial stretch of the liner body 242 and/or outer cover. In addition, the friction material of the seal bands 256 can reduce the likelihood of relative axial movement between the liner body 242 and the socket, improving suspension and/or reducing pistoning.

Figure 27:
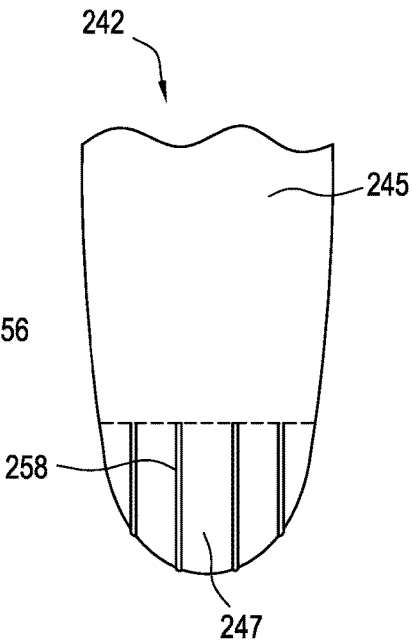

FIG. 27 offers another variation of a plurality of seal bands 258 similar to the seal bands 256 except that the seal bands 258 only extend along a distal portion 247 of the liner body 242. According to a variation, the seal bands 258 can decrease the axial stretch and/or the coefficient of friction of the distal portion 247 relative to the proximal portion 245 of the liner body 242. It will thus be appreciated that the seal bands 258 can be positioned in certain regions of the liner body 242 to beneficially influence different characteristics of the liner body 242 and/or suspension of the socket on the liner body.

Figure 28:
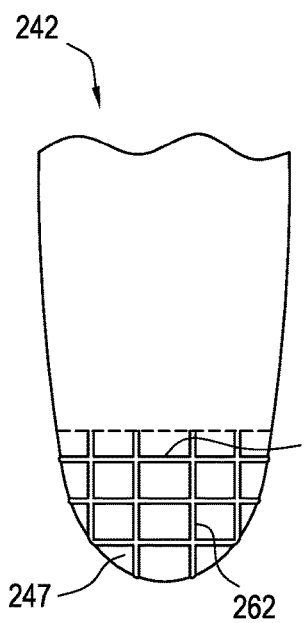

FIG. 28 offers another variation of a first plurality of seal bands 260 extending horizontally about a circumference of the liner body 242 at the distal portion 247, and a second plurality of seal bands 262 extending in a generally axial direction at the distal portion 247. As seen, the first seal bands 260 and second seal bands 262 can form a grid-like pattern at the distal portion 247 of the liner body 242. This arrangement can increase the frictional engagement between the liner body and a socket, and provide both axial and radial stiffness to the distal portion 247 of the liner body 242, helping to control movement between the distal end of a residual limb and the socket.

Figure 29:
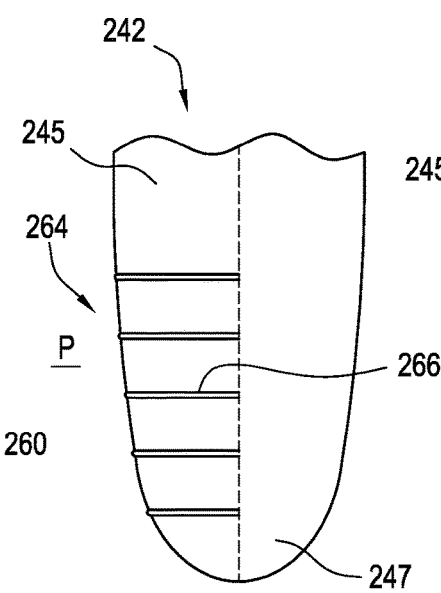

FIG. 29 offers another variation including a region of seal bands 264 located along a length of the liner body 242 on a posterior area P of the liner body 242. The seal bands 264 can extend along the distal portion 247 and at least a portion of the proximal portion 245. The seal bands 264 can extend along the distal portion 247. In an embodiment, the liner body 242 can be a transtibial liner and the region of seal bands 264 can include a plurality of partial ring segments 266 generally oriented in a horizontal direction that influence how the liner bends under knee flexion.

Figure 30:
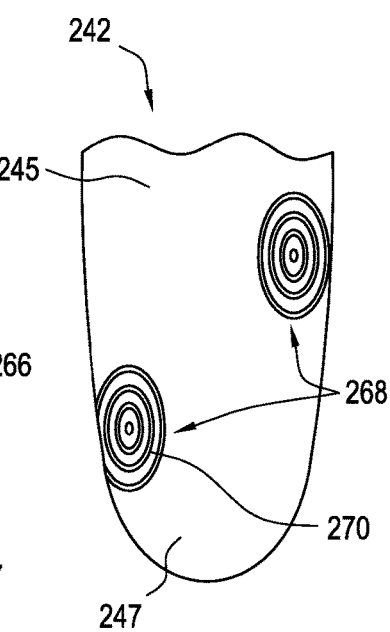

FIG. 30 offers another variation including a plurality of discrete regions 268 of seal bands. Each region 268 can include a grouping of concentric rings 270. The liner body 242 can include a first region 268 of seal bands on the proximal portion 245 and a second region 268 of seal bands on the distal portion 247. In other embodiments, the liner body 242 can include more or fewer regions 268 of seal bands. Further, the regions 268 of seal bands can be located at any suitable location on the liner body 242.

The regions 268 of seal bands increase the coefficient of friction between the liner body 242 and a socket, improving suspension. The regions 268 may also provide rotational control when the liner body 242 is inserted into a socket. For instance, the regions 268 of seal bands may include frictional material to minimize rotational movement of the liner body relative to the socket.

Figure 31:
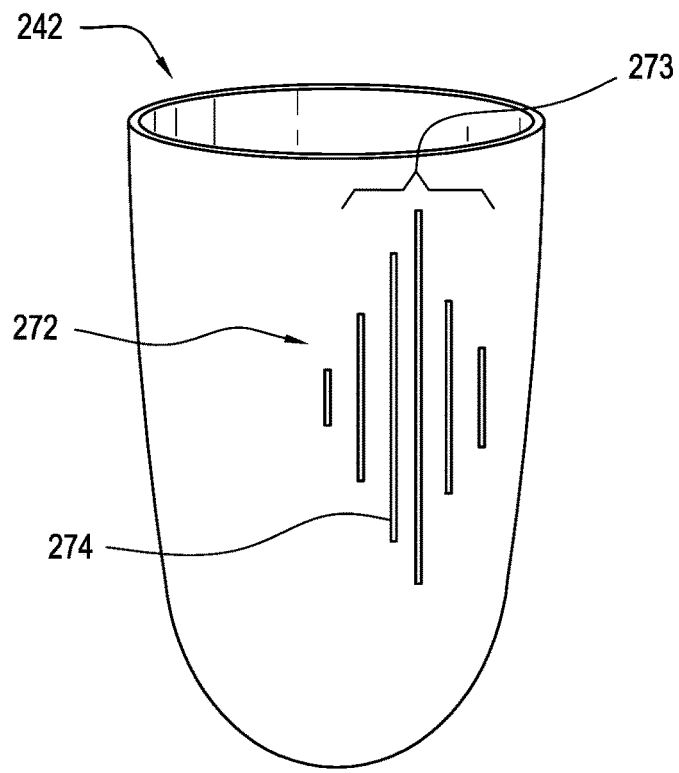

FIG. 31 offers another variation including a region 272 of seal bands 274 disposed on a portion of the liner body 242. The seal bands 274 include a plurality of axial bands 274, each increasing in length toward a center 273 of the region 272. The region 272 of seal bands may include frictional material to minimize rotational and/or axial movement of the liner body 242 relative to the socket.

Figure 32:
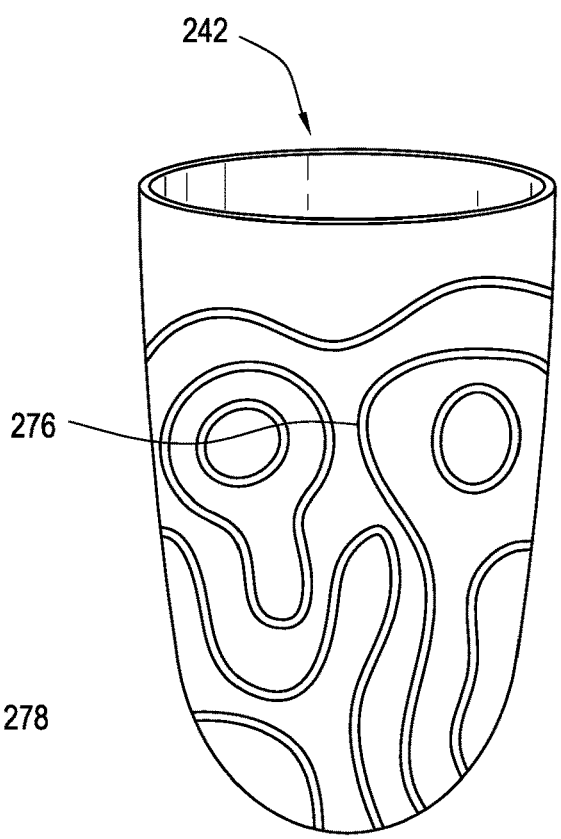

FIG. 32 offers another variation including a plurality of seal bands 276 arranged in one or more anatomical patterns on the liner body 242. For instance, the seal bands 276 can be arranged in patterns for interfacing with the anatomy of user's thigh or lower leg, providing cushioning and/or stabilization to targeted regions of the residual limb.

Figure 33:
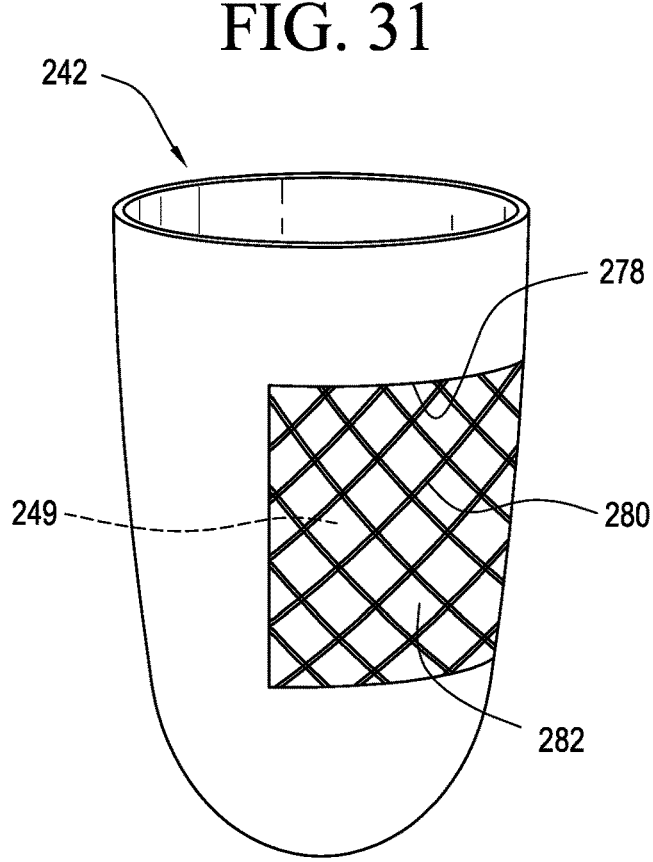

FIG. 33 offers another variation including a liner body 242 defining an opening 278 in communication with an interior 249 of the liner body 242. The opening 278 can have any suitable size and/or shape and can be located in any suitable portion of the liner body 242. A plurality of seal bands 280 can be attached to the liner body 242 and extend across the opening 278 in a cross-hatch or mesh pattern. This is advantageous because the seal bands 280 can influence the characteristics of the liner body 242 and the interaction between the liner body 242 and a socket while also defining smaller openings 282 in communication with the interior 249 of the liner body 242, making at least a section of the liner body 242 breathable, improving comfort and/or moisture control.

Figure 34:
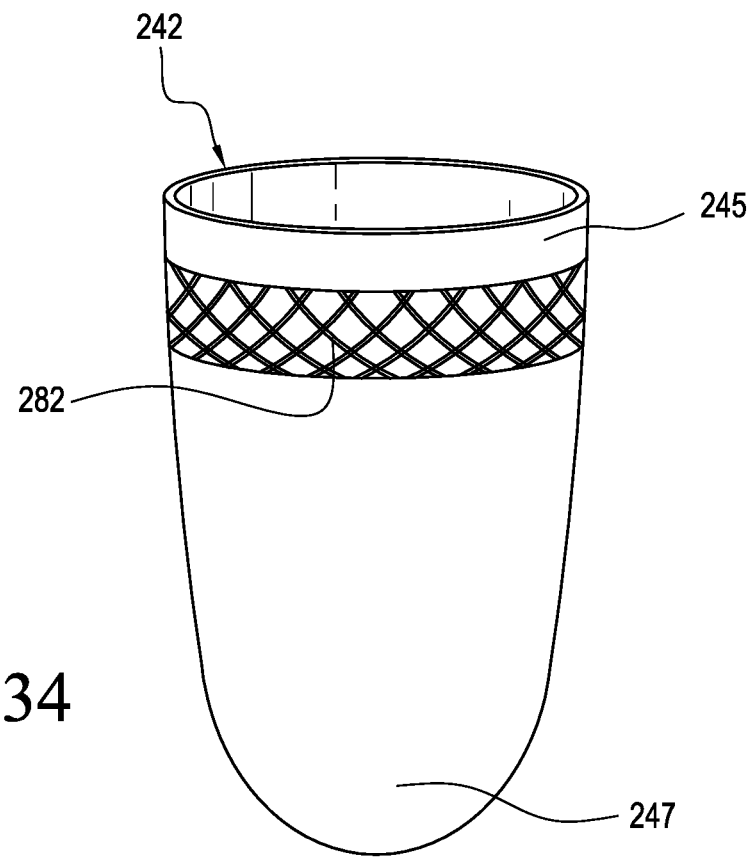

FIG. 34 offers another variation of a plurality of seal bands 282 in a cross-hatch pattern extending around the proximal portion 245 of the liner body 242. The seal bands 282 can provide additional thickness and/or hardness to the proximal portion 245. This is advantageous as the seal bands 282 can protect the liner body 242 from the proximal edge of a socket, increasing the durability of the liner body 242.

Figure 35:
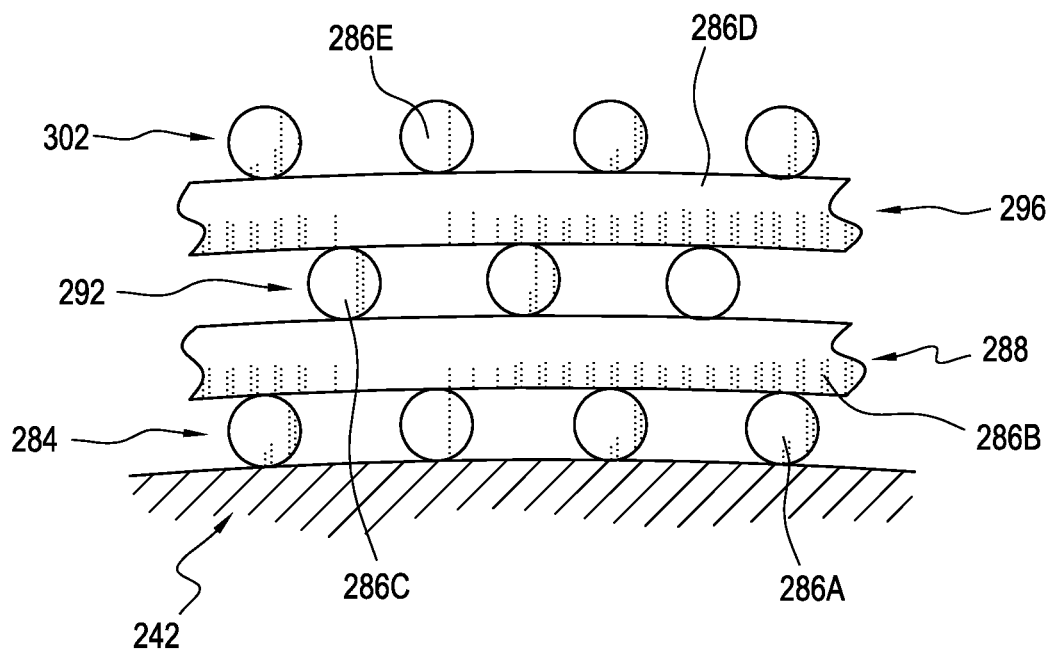

FIG. 35 offers another variation of seal bands 286 forming a three-dimensional structure on the liner body 242. The seal bands can be arranged in a first layer 284 having a first plurality of seal bands 286A extending in a first direction. The first layer 284 can be attached to or integral to the liner body 242. A second layer 288 can be positioned on the first layer 284. The second layer 288 includes a second plurality of seal bands 286B extending a second direction that is generally normal or oblique relative to the first direction. The second layer 288 can be attached to or integral to the first layer 284, forming a three-dimensional structure. A third layer 292 of a third plurality of seal bands 286C can be positioned on and attached to or integral to the second layer 288. The third seal bands 286C can generally extend in the first direction. A fourth layer 296 of a fourth plurality of seal bands 286D can be positioned on and attached to or integral to the third layer 292. The fourth layer can extend generally in the second direction. A fifth layer 302 of a fifth plurality of seal bands 286E can be positioned on and attached to or integral to the fourth layer 296, completing the three-dimensional structure.

The three-dimensional structure can form a reinforcement layer, helping to prevent elongation of tissue of the residual limb fitted with the socket. The three-dimensional structure can also beneficially define a breathable layer on the liner body 242.

The placement of the three-dimensional structure is not limited to a specific area of the liner body 242, and may extend upwardly to the proximal end of the liner body 242. Further, while five layers of seal bands are shown and described to complete the three-dimensional structure, the three-dimensional structure can be formed with two, three, four, or any other suitable number of layers. Moreover, one or more of the different layers of seal bands can be interwoven. It will be appreciated that any of the cross-hatch or mesh patterns of the seal bands described herein may form a three-dimensional structure.

Figure 36:
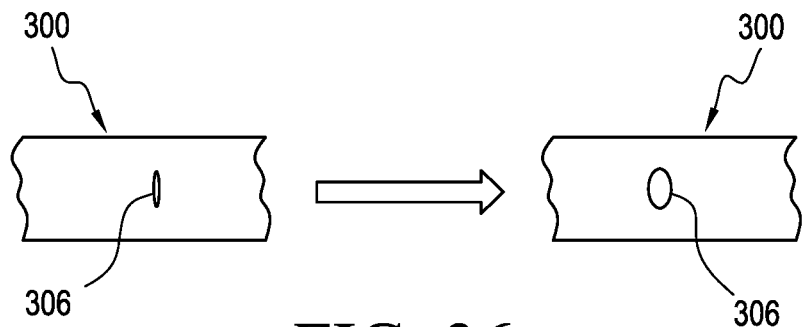
FIGS. 36-38 are schematic views of a tension indicator according to various embodiments.
Figure 37:
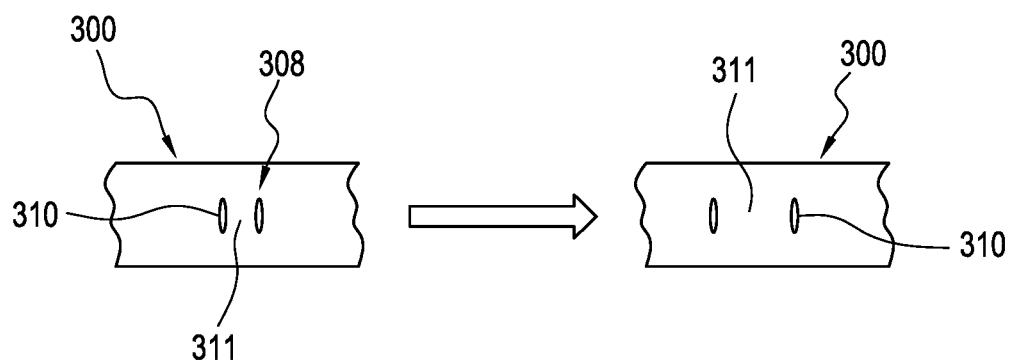
Figure 38:
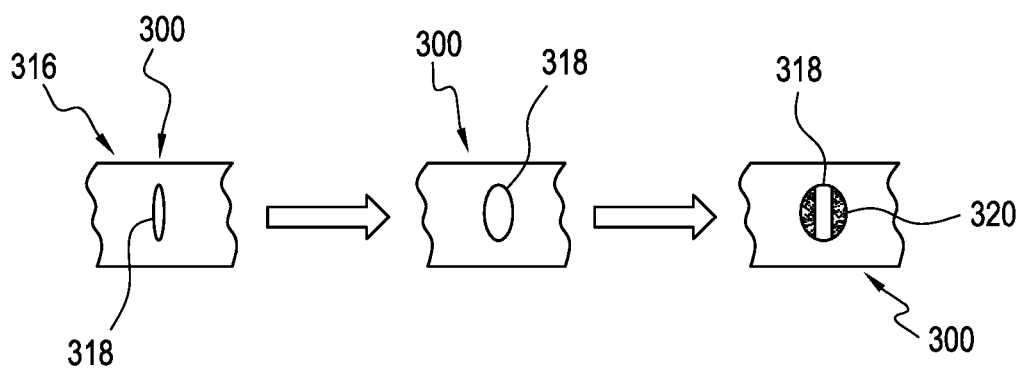
Figure 42:
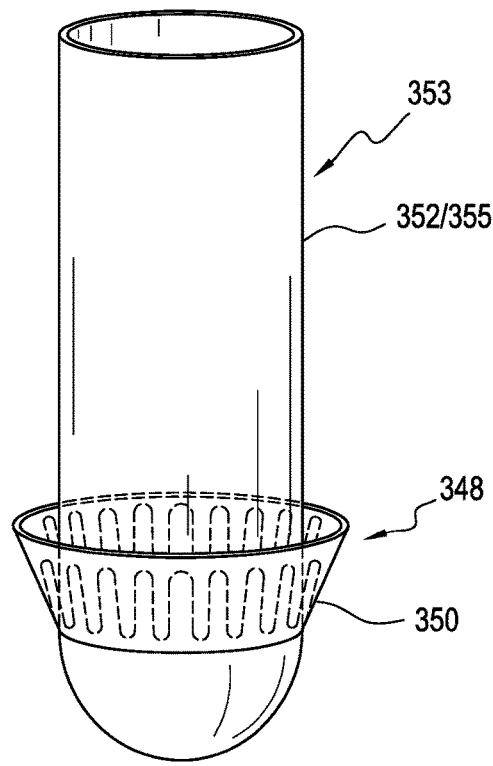
FIG. 42 is an isometric view of a seal system according to another embodiment.
Figure 43:
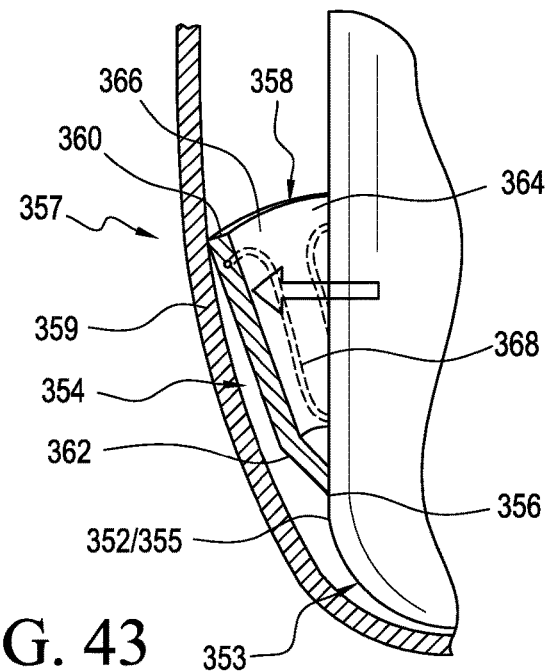
FIG. 43 is a cross-section of the seal component of FIG. 42 according to an embodiment.
Figure 44:
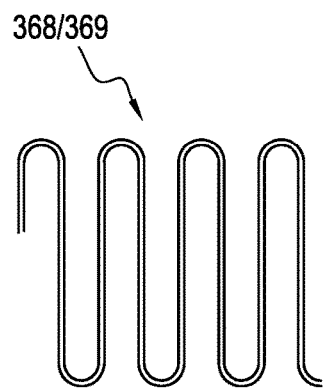
FIG. 44 is a partial view of the seal member of FIG. 42.

FIGS. 36-38 illustrate variations of pressure or tension indicators associated with the seal bands. The pressure or tension indicators advantageously can indicate if there is excessive or insufficient tension about the seal bands. FIG. 36 illustrates a variation of a tension indicator 306 incorporated in a seal band 300. In this embodiment, the tension indicator 306 includes a recess that opens when the seal band 300 is tensioned. It will be appreciated that the tension indicated by the tension indicator 306 can be axial tension and/or radial tension depending on the orientation of the seal band 300.

FIG. 37 illustrates another variation of a tension indicator 308 including a pair of elongate recesses 310 incorporated in the seal band 300. In this embodiment, the elongate recesses 310 move apart, increasing a space 311 defined therebetween, when the seal band 300 is tensioned or over tensioned, providing a visual indication to a user that the seal band 300 is in tension. An increase in size of the space 311 from an original size can correspond to an increase in tension in the seal band 300. As such, a larger space 311 between the recesses 310 indicates a higher level of tension in the seal band 300. A smaller space 311 between the recesses 310 indicates a lower level of tension in the seal band 300. It will be appreciated that the recesses 310 can have any suitable shape. For instance, the recesses can have a circular or other shape that moves apart when the seal band 300 is tensioned or over tensioned.

FIG. 38 illustrates another variation of a tensioner indicator 316 including a recess 318 incorporated in the seal band 300. In the illustrated embodiment, the recess 318 partially opens when the seal band 300 is tensioned, and completely opens when the seal band 300 is fully tensioned or over tensioned thereby exposing a colored portion 320 found in the recess 318. This beneficially provides a straightforward mechanism for conveying tension levels in the seal band 300 to a user.

In each of the embodiments described herein, the adjustable seal system permits optimal seal placement rather than a permanently fixed seal placement as found in many prior art seal systems. The seal components may be located away from undercuts or shape irregularities defined by a residual limb. The seal height may be decided according to the user's needs, and the seal may be moved to adapt to various volume changes of the residual limb. In some embodiments, the adjustable seal system beneficially assists users with seal placement on a liner body, improving its ease of use.

The adjustable seal system embodiments require less effort when donning the liner. For example, rather than deal with a permanent seal resisting donning, the liner may be donned and then the seal may be selectively placed along the height of the liner worn by the user.

The adjustable seal embodiments provide improved comfort for the user. The seal height may be decided according to the needs of the user, and sensitive areas may be avoided. The embodiments make it possible to provide temporary relief of pressure below the seal. Because the seal is adjustable, the distal end of the liner may have improved conformability since it does not require being configured with a permanent seal but rather is uninhibited by such structural limitations found in the prior art. For example, the embodiments of the adjustable seal system enable improved proximal support since the liner may be arranged in a longer configuration over prior art liners, and improved proprioception may be obtained since the distal end may be arranged thinner with better linkage to the socket over prior art liners. Due to the seal bands of the liner, there is improved rotational control of the liner and seal relative to the socket.

The adjustable seal embodiments may enable improved durability by having better abrasion resistance due to the versatility in placement of the seal component and its separate yet non-permanent attachment to the liner.

In some embodiments, the seal system can include one or more seal-assist features or systems. FIGS. 39-41 show another embodiment of a seal system 322 including a seal component 324 on a liner body 326 of a liner sleeve. The seal component 324 includes at least one resilient seal member 328 protruding radially from the liner body 326. The at least one seal member 328 may extend either partially or entirely around an outer peripheral portion of the liner body 326. The at least one seal member 328 includes a root 330 extending from the liner profile and a section 332 projecting from the root 330 and terminating at a peak 334. The section 332 can have a cantilevered configuration. The profile of the section 332 may be linear, arcuate, curvilinear, and may include one or more sections.

A variable clearance 336 is defined between the section 332 and the liner profile. The at least one seal member 328 is arranged for deflection towards the liner profile of the liner body 326 when donned on a residual limb and placed within a prosthetic socket 338.

The at least one seal member 328 may be formed in accordance with any of the embodiments described herein. The seal component 324 can be separate from or integral to the liner body 326.

The at least one seal member 328 can include a seal-assist system to help force or maintain the at least one seal member 328 against an interior wall of the socket. For instance, material forming the at least one seal member 328 can include one or more magnetic materials or particles 340 as seen in FIGS. 39 and 40. The magnetic materials 340 may extend within the seal member either partially or entirely around an outer peripheral portion of the liner body 326. Preferably, the magnetic materials 340 extend within the seal member entirely around the outer peripheral portion of the liner body 326.

Optionally, at least one magnetic member 342 such as a wire may be embedded or attached to the at least one seal member 328 as seen in FIGS. 39 and 41. The magnetic member 342 may extend within the seal member either partially or entirely around the outer peripheral portion of the liner body 326. The magnetic member 342 may include a plurality of flexible coils or bends, increasing the length of the wire within the at least one seal member 328 and optionally providing resiliency to the magnetic member 342.

Referring to FIG. 39, a ring or annular band member 344 may be installed on the outer surface of the socket 338 in the general area of the at least one seal member 328. The band member 344 may include one or more permanent magnets 346 and/or ferromagnetic material circumferentially distributed within the band member 344. In other embodiments, the magnets 346 may be attached to an exterior or interior surface of the at least one seal member 328.

In use, the at least one seal member 328 is held or pulled away from the liner body 326 and/or against the inner surface of the socket 338 by magnetic attraction between the at least one seal member 328 and the band member 344 when the liner is inserted into the socket 338. This beneficially increases the radial sealing forces between the at least one seal member 328 and the inner surface of the socket wall 327, improving the connection between the liner and the socket. Further, the magnetic force or attraction between the seal member 328 and the inner surface of the socket wall 327 of the socket can be customized based on the individual needs of the user. For instance, the magnetic strength of the permanent magnets 346 can be selected to vary the magnetic attraction between the seal member 328 and the inner surface of the socket wall 327 of the socket based on activity level.

Optionally, the band member 344 may be omitted. For instance, one or more permanent magnets 346 and/or ferromagnetic material may be included in the socket wall 327. In another variation, the at least one seal member 328 may include one or more ferromagnetic materials and the socket wall 327 or band may include permanent magnets and/or magnetic materials.

FIGS. 42-46 show another embodiment of a seal system 348 including a seal-assist system. The seal system 348 includes a seal component 350 on a liner body 352 of a liner sleeve 353. The seal component 350 includes at least one resilient seal member 354 protruding radially from the liner body 352. The at least one seal member 354 may extend either partially or entirely around an outer peripheral portion of the liner body 352.

The at least one seal member 354 includes a root 356 extending from the liner profile 355 and a section 358 projecting from the root 356 and terminating at an upper edge 360. The section 358 can include a lower flexible wall portion 362 and an upper generally upright wall portion 364. A variable clearance 366 is defined between the section 358 and the liner profile 355. Like the seal member 328, the at least one seal member 354 is arranged for deflection towards the liner profile 355 of the liner body 352 when donned on a residual limb and placed within a prosthetic socket. It will be appreciated that the at least one seal member 354 may be formed in accordance with any of the embodiments described herein. The seal component 350 can be separate from or integral to the liner body 352.

Figure 45:
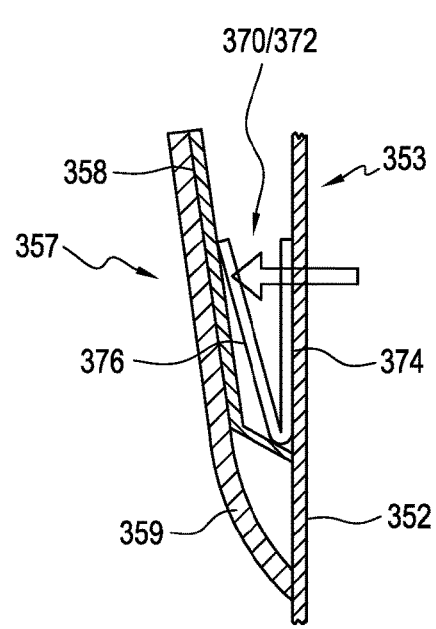
FIG. 45 is a cutaway view of the seal member of FIG. 42 according to another embodiment.

Like the previous embodiment, the at least one seal member 354 can include a seal-assist system to help force or maintain the at least one seal member 354 against an inner surface of a socket wall. For instance, a resilient element 368 can be associated with the at least one seal member 354. The resilient element 368 can be disposed within the section 358 of the at least one seal member 354. The resilient element 368 may extend either partially or entirely around the outer peripheral portion of the liner body 352. The resilient element 368 can be made from metal, plastic, and/or any other suitable material. In the illustrated embodiment, the resilient element 368 can comprise a spring member 369 including a plurality of coils or bends as seen in FIG. 45.

When the liner 353 is inserted into a socket 357, the spring member 369 is compressed and biases or forces the at least one seal member 354 radially outward relative to the liner body 352, toward the inner surface of the socket wall 359. More particularly, the spring member 368 can be compressed between the liner body 352 and the socket wall 359 and the stored mechanical energy in the spring member 368 can force the at least one seal member 354 radially outward against the socket wall 359, improving the connection between the liner and the socket.

Further, because the spring member 368 is disposed within the section 358, pressure exerted on the residual limb by the spring member 368 is reduced, providing a more comfortable fit. In other embodiments, the spring member 368 can be located on an exterior or interior surface of the at least one seal member 354.

The resilient element 368 is described as a spring member 369 however other resilient elements are possible. For instance, FIG. 45 shows a variation of a resilient element 370 including a v-type spring 372 including a first arm 374 engaging the liner body 352 and a second arm 376 engaging an interior surface of the section 358 of the at least one seal member 354. The resilient element 370 can be compressed between the liner body 352 and an inner surface of the socket wall 359 and the stored mechanical energy in the resilient element 370 can force the at least one seal member 354 radially outward against the socket wall 359, improving the connection between the liner 353 and the socket 357. In another variation, the v-type spring can be disposed within a thickness of the section 358 of the seal member.

Figure 46:
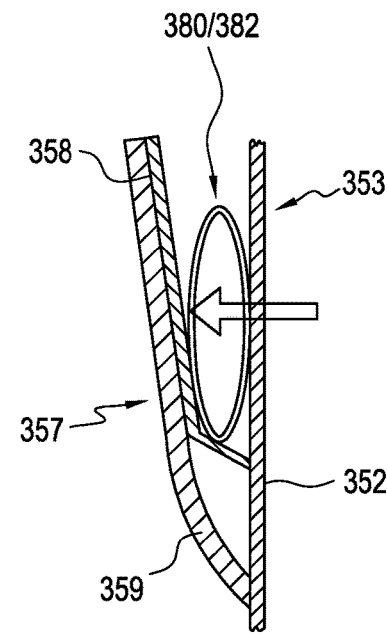
FIG. 46 is a cutaway view of the seal member of FIG. 42 according to another embodiment.

FIG. 46 shows a variation of a resilient element 380 including an elliptical member 382 having a hoop configuration. Similar to the previous embodiment, the elliptical member 382 can be compressed between the liner body 352 and an inner surface of the socket wall 359 and the stored mechanical energy in the elliptical member 382 can force the at least one seal member 354 radially outward relative to the liner body 352 and against the socket wall 359, improving the connection or sealing forces between the liner 353 and the socket 357. In another variation, the elliptical member 382 can be disposed within the section 358 of the seal member.

In other variations, the resilient element can comprise any suitable member to force the seal member toward the interior wall of a socket, such as, for example a torsion spring or bar or any other suitable member.

While the foregoing embodiments have been described and shown, alternatives and modifications of these embodiments, such as those suggested by others, may be made to fall within the scope of the invention. For instance, the adjustable seal system embodiments may include any adjustable seal components as described in U.S. patent application Ser. No. 14/541,505, incorporated by reference and belonging to the assignee of this disclosure. Further, the principles described may be extended to other types of prosthetic devices. In yet other embodiments, the seal components can be arranged to secure on an outer surface of a liner without seal bands.

The invention claimed is:

1. A suspension liner including a liner body defining a liner profile along an exterior periphery thereof, the suspension liner comprising:
- at least one resilient seal member protruding radially from the liner body, the at least one resilient seal member extending at least partially around the exterior periphery of the liner body, the at least one resilient seal member having a section projecting from a root extending from the liner profile, and the section extending away from the root and terminating at an upper edge of the at least one seal member, the section including a lower flexible wall portion and an upper generally upright wall portion protruding outwardly away and obliquely relative to the lower flexible wall portion, the upper generally upright wall portion having a linear profile terminating at the upper edge;
- wherein a variable clearance is defined between the at least one resilient seal member and the liner profile such that the upper generally upright wall portion of the at least one resilient seal member is arranged for deflection towards the liner profile of the liner body;
- a resilient element in correspondence with the at least one resilient seal member by extending parallel to at least the upper generally upright wall portion, the resilient element being a spring member including a plurality of bends arranged according to the upper generally upright wall portion so as to be directed toward the upper edge of the at least one resilient seal member and a connection of the upper generally upright wall portion to the lower flexible wall portion, the resilient element extending above the lower flexible wall portion and only corresponding to and contained within the upper generally upright wall portion;
- wherein the resilient element is embedded within and surrounded by a thickness of the upper generally upright wall portion, the resilient element extending within the upper generally upright wall portion between the upper edge and the lower flexible wall portion, the resilient element including a plurality of elongate sections extending parallel to a length of the upper generally upright wall portion, and between the bends; the bends extend parallel to the thickness of the resilient element the elongate sections are longer than the bends;
- wherein the at least one resilient seal member is formed from silicone, and the resilient element is formed from a material different from silicone and selected from the group consisting of metal and plastic;
- wherein the upper edge of the at least one resilient seal member is spaced apart from the resilient element.

2. The suspension liner of claim 1, wherein the resilient element extends entirely around the exterior periphery of the liner body.

3. The suspension liner of claim 1, wherein the resilient element is arranged to compress and bias the at least one resilient seal member radially outward relative to the liner body.

4. The suspension liner of claim 1, wherein the resilient element is arranged to compress and store mechanical energy to force the at least one resilient seal member radially outward.

* * * * *